(12) United States Patent
Murakami et al.

(10) Patent No.: US 8,142,660 B2
(45) Date of Patent: Mar. 27, 2012

(54) FILTRATE MONITORING DEVICE, AND FILTRATE MONITORING SYSTEM

(75) Inventors: Seigo Murakami, Kumamoto (JP); Takenori Hirakawa, Kumamoto (JP); Takafumi Iseri, Kumamoto (JP)

(73) Assignee: Hirata Corporation, Tokyo (JP)

( * ) Notice: Subject to any disclaimer, the term of this patent is extended or adjusted under 35 U.S.C. 154(b) by 472 days.

(21) Appl. No.: 12/445,350

(22) PCT Filed: Oct. 19, 2007

(86) PCT No.: PCT/JP2007/070491
§ 371 (c)(1),
(2), (4) Date: Apr. 13, 2009

(87) PCT Pub. No.: WO2008/047926
PCT Pub. Date: Apr. 24, 2008

(65) Prior Publication Data
US 2010/0097605 A1    Apr. 22, 2010

(30) Foreign Application Priority Data
Oct. 19, 2006  (JP) ................. 2006-284781

(51) Int. Cl.
*B01D 35/00*   (2006.01)
*C02F 1/44*   (2006.01)

(52) U.S. Cl. ............ 210/637; 210/644; 210/87; 210/86; 210/93; 210/96.2

(58) Field of Classification Search .................. 210/637, 210/95
See application file for complete search history.

(56) References Cited

U.S. PATENT DOCUMENTS

| | | | |
|---|---|---|---|
| 2002/0051992 A1 | 5/2002 | Bridgham et al. | |
| 2010/0126940 A1* | 5/2010 | Ryu et al. | 210/744 |

FOREIGN PATENT DOCUMENTS

| | | | |
|---|---|---|---|
| JP | 1993-215664 A | | 8/1993 |
| JP | 1994-035948 A | | 5/1994 |
| JP | 1995-086457 B | | 9/1995 |
| JP | 1996-11996-146299 A | | 6/1996 |
| JP | 1996-252440 A | | 10/1996 |
| JP | 1998-024283 A | | 1/1998 |
| JP | 2000-046721 A | | 2/2000 |
| JP | 2000046721 A | * | 2/2000 |
| JP | 2000-088841 A | | 3/2000 |
| JP | 2000-155088 A | | 6/2000 |
| JP | 2000-342937 A | | 12/2000 |
| JP | 2000342937 A | * | 12/2000 |
| JP | 2002-082025 A | | 3/2002 |
| JP | 2004-216311 A | | 8/2004 |
| JP | 2005-013992 A | | 1/2005 |

* cited by examiner

*Primary Examiner* — Krishnan S Menon
*Assistant Examiner* — Allison M Gionta
(74) *Attorney, Agent, or Firm* — Trojan Law Offices

(57) ABSTRACT

A filtrate monitoring device and a filtrate monitoring system, which can monitor a membrane-type water filtrating/purifying system at all times and which can flexibly adjust themselves to the contents and sizes of impurities, are provided. The filtrate monitoring device monitors the filtrate having passed through the membrane-type water filtrating/purifying device. The filtrate monitoring device comprises: imaging/detecting means for shooting images in the filtrate having passed through the filtrating/purifying device, on the filtrate flowing in an observation bath of a filtrate observing cell disposed midway of the branched filtrate pipeline, thereby to specify the particles contained in the filtrate, and/or optical detecting means disposed midway of the filtrate pipeline before or after branching.

18 Claims, 16 Drawing Sheets

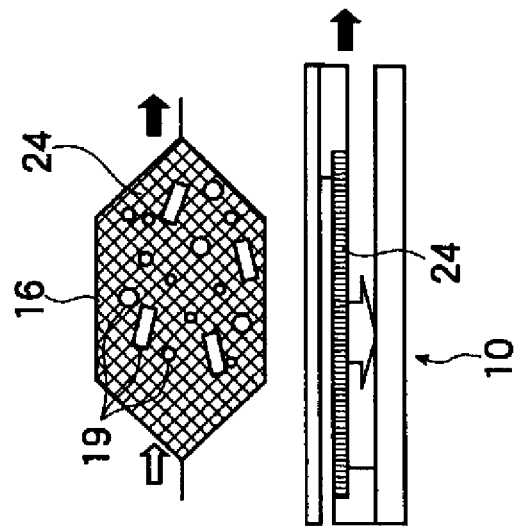
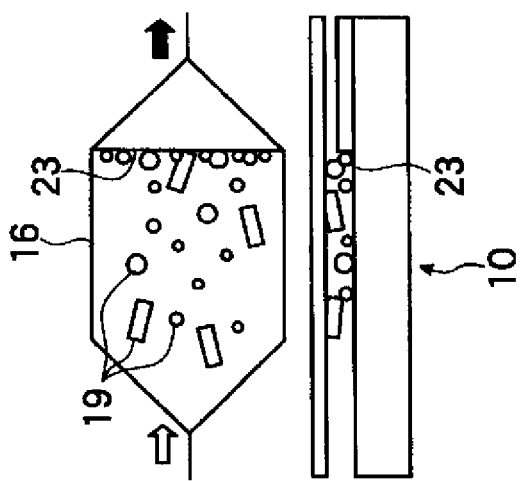
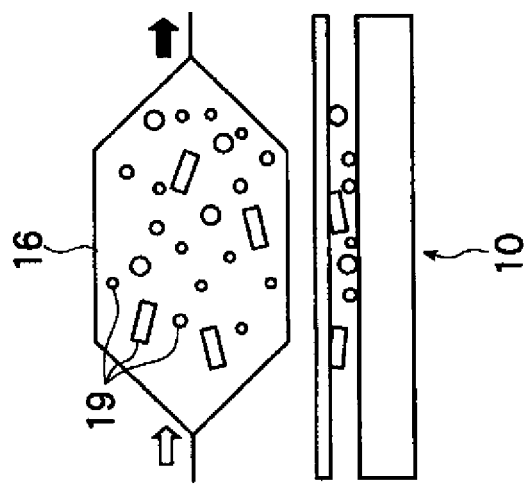

Flow path plate

In a state that bead particles accumulated
in a predetermined place on the plate

FIG. 12

FILTRATE MONITORING DEVICE, AND FILTRATE MONITORING SYSTEM

PRIORITY CLAIM TO RELATED APPLICATION

This application is based upon and claims the benefits of priority from Japanese Patent Application No. 2006-0284781 filed on Oct. 19, 2006, the entire contents of which are incorporated herein by reference.

FIELD OF THE INVENTION

The present invention relates to a membrane filtration water-purifying apparatus in order to purify water from any type of water source including river water, lake water, or groundwater, and to a filtrate water monitoring apparatus and a filtrate water monitoring system in a membrane filtration water-purifying system.

BACKGROUND ART

As water-purifying equipment for filtrate plants that purifies natural water into clean water, water-purifying equipment in which coagulation settling tanks and sand filtration equipment are combined have been conventionally used in a large number of applications. There are issues with such equipment that the equipment tends to be large in scale, a construction cost thereof is high, automation thereof is difficult, operation and management thereof are not easy, many chemicals such as aggregating agents are added thereto, it is difficult to improve water quality, and so on. Recently, various membrane filtration water-purifying systems using high-performance filtration films have been proposed and implemented as alternative equipment.

In such a membrane filtration water-purifying system, the performance and lifetime of a filtration film serving as a filtration medium are factors of key importance. From this point of view, the development of a high-quality filtration film and the development of a simple monitoring system that detects damage to a filtration medium and monitors its performance degradation have been in demand.

As a filtration film, a film called a hollow-fiber membrane module has been conventionally developed and used. This is a film in which several thousands to several tens of thousands of hollow fibers are bundled and housed in a case housing to form a module. As a system for monitoring performance degradation by damage thereto; a system in which an optical sensor is equipped so as to sense bubbles generated by making air invading from the outside to the inside of a hollow-fiber membrane; a system in which a gaseous body including fine particles is made to flow into a hollow-fiber membrane module, and a number of fine particles in the gaseous body passing through the hollow-fiber membrane is measured by a fine particle meter equipped with a laser light source; a system in which a secondary side of a hollow-fiber membrane is made into a full-capacity state with water, a given gaseous body is pressure-fed from a primary side, and a quantity of water pushed out from the primary side to the secondary side of the hollow-fiber membrane is measured after the pressure of the gaseous body is kept a certain pressure for a given time, and so on have been proposed to apply to various methods and apparatuses (for example, Patent Documents 1 to 4).

A water quality meter attached to a part of a distributing water pipe of water works distributing water system is also disclosed wherein the meter comprises an analyzer that analyzes sample water guided from the distributing water pipe and a guiding part composed of a single member having a plurality of supply channels for supplying a plurality of liquids including the sample water in the analyzer (for example, Patent Document 5). Further, a particle diameter distribution measuring apparatus comprising a sample liquid circulating system and a sample liquid measuring system is disclosed wherein the apparatus is improved by adding a step of applying ultrasonic to the conventional drain method such that a frequency of cleaning cycles and an amount of waste fluid are decreased (for example, Patent Documents 6 and 7).

Moreover, a method comprising the steps of detecting weight of insoluble fine particles utilizing that the laser beam is scattered by the insoluble fine particles and judging the completion of dissolution is disclosed (for example, Patent Document 8).

Further, a detection method comprising the steps of collecting optical beams from a coherent light source, focusing the beams on something in a flow of liquid including fine particles, detecting a change of diffracted light generated in the optical beams, and measuring the number of fine particles is disclosed (for example, Patent Document 9). Further, a measurement method for measuring fine particles in liquid comprising the steps of irradiating a laser beam inside a fluid liquid, detecting scattered light from fine particles floating in the liquid, and measuring characteristics of the particles such as particle diameters and the number of particles is disclosed (for example, Patent Document 10).

However, those are implemented as the operation of the membrane filtration water-purifying system is temporarily stopped such that it is not possible always to monitor the water. Further, in case that impurities in the flow channel of the filtrate water pipe line system is too few, or that impurities are unevenly dispersed in the flow channel, it may not be possible to shoot and analyze images therein. Further, those are not designed for detecting damage to the filtration film, and configurations thereof are different. Then, it is difficult to identify ruptured pieces of the film since images including various sizes of mixed impurities are detected when the film is broken.

[Patent Document 1] JP-A-2000-342937
[Patent Document 2] JP-A-2004-216311
[Patent Document 3] JP-A-2005-013992
[Patent Document 4] JP-A-H10-024283
[Patent Document 5] JP-B-3551073
[Patent Document 6] JP-A-2000-155088
[Patent Document 7] JP-U-A-H06-35948 (Utility Model)
[Patent Document 8] JP-A-2002-82025
[Patent Document 9] JP-B-3151036
[Patent Document 10] JP-B-H07-86457

DISCLOSURE OF THE INVENTION

Problem to be Solved by the Invention

Now, it is an object to provide a filtrate water monitoring apparatus and a filtrate water monitoring system which are capable of always monitoring a membrane filtration water-purifying system, and flexibly responding to an amount or a size difference of impurities.

Means for Solving the Problem

The present invention has been conceived in consideration of the above-described issues. It is embodied as a filtrate water monitoring apparatus which monitors filtrate water discharged from a membrane filtration water-purifying apparatus and the filtrate water monitoring apparatus comprises image detection means for shooting an image in filtrate water which flows in an observation bath of a filtrate water observation cell disposed midway of a branch filtrate water pipe line system branched therefrom where the filtrate water is discharged from the membrane filtration water-purifying apparatus and for identifying particles in flowing water included in the filtrate water; and/or optical detection means which is provided midway of the filtrate water pipe line system before or after branching.

More specifically, the following may be provided.

(1) A filtrate water monitoring apparatus which monitors filtrate water discharged from a membrane filtration water-purifying apparatus may be provided. The filtrate water monitoring apparatus comprises: physical detection means for utilizing or detecting a physical phenomenon which varies depending on behavior of particles in the filtrate water flowing in a branch filtrate water pipe line system (hereinafter, called "particles in flowing water") wherein the physical detection means is connected to the branch filtrate water pipe line system branching in order to sample some of the filtrate water as sample water from a filtrate water pipe line system connected to an outlet of the membrane filtration water-purifying apparatus; a filtrate water observation cell which is arranged downstream of the physical detection means in the branch filtrate water pipe line system and has a flow channel for letting the filtrate water pass through inside thereof; and image detection means for shooting an image in filtrate water flowing in the flow channel of the filtrate water observation cell and for identifying impurities included in the filtrate water.

Here, the behavior of the particles in the flowing water may include movement as an individual particle, a movement as a cluster due to several particles move collectively, and the like. Further, a variable physical phenomenon depending on such behavior may include changes in an electromagnetic wave such as light, electrical and electrochemical changes, and mechanical changes such as water pressure. This change in the light may mean light emitted from the particles or light emitted from one or more light sources other than the particles are subject to changes in the wavelength (including a long or short change and/or a change in wavelength distribution), and/or a change in the intensity and/or a change in the quantity by scattering or interference by these particles. Accordingly, for example, optical detection means for detecting light released or transmitted in spite of blockage caused by scattering or interference of particles in the flowing water, or other optical detection devices may be included. Further, optical detection means for detecting scattered light, or blocked or transmitted light by particles in flowing water as light is irradiated in the middle of a filtrate water pipe line system before branching or after branching may be included. More specifically, a so-called optical particle counter may be included. Further, electrical sensing means such as a Coulter counter may be included in addition to detection means utilizing light.

(2) The filtrate water monitoring apparatus according to the above (1) may be provided, wherein the physical detection means is a turbidity meter with a laser beam.

(3) The filtrate water monitoring apparatus according to the above (1) may be provided, wherein the physical detection means is a fine-particle counter with a laser beam.

(4) The filtrate water monitoring apparatus according to any one of the above (1) to (3), comprising: an openable and closable valve disposed between the physical detection means and the filtrate water observation cell in the branch filtrate water pipe line system is provided such that the filtrate water flows into the filtrate water observation cell when the physical detection means detects a greater number of particles in the flowing water than a predetermined number.

(5) The filtrate water monitoring apparatus according to the above (4) may be provided, wherein the image detection means identifies the particles in the flowing water after a predetermined period of time from when the physical detection means detects the greater number of particles in the flowing water than the predetermined number.

(6) The filtrate water monitoring apparatus according to any one of the above (1) to (5) may be provided, as being characterized by comprising: physical concentration means for increasing density of the particles in the flowing water that flows into the filtrate water observation cell, the physical concentration means disposed between the physical detection means and the filtrate water observation cell in the branch filtrate water pipe line system.

(7) A filtrate water monitoring apparatus which monitors filtrate water discharged from a membrane filtration water-purifying apparatus may be provided, as being characterized by comprising: a filtrate water observation cell connected to a branch filtrate water pipe line system which branches for sampling part of the filtrate water as sample water from the filtrate water pipe line system connected to an outlet of the membrane filtration water-purifying apparatus, the filtrate water observation cell having inside a flow channel in which the filtrate water flows, and image detection means for shooting an image in the filtrate water flowing in the flow channel of the filtrate water observation cell so as to identify the particles in the flowing water included in the filtrate water, wherein the filtrate water observation cell has an observation bath through which flow of the filtrate water is observed in the flow channel, and a plurality of filtrate water observation cells are arranged in series along the branch filtrate water pipe line system.

(8) A filtrate water monitoring apparatus which monitors filtrate water discharged from a membrane filtration water-purifying apparatus may be provided, as being characterized by comprising: a filtrate water observation cell connected to a branch filtrate water pipe line system which branches for sampling part of the filtrate water as sample water from the filtrate water pipe line system connected to an outlet of the membrane filtration water-purifying apparatus, the filtrate water observation cell having inside a flow channel in which the filtrate water flows, and image detection means for shooting an image in the filtrate water flowing in the flow channel of the filtrate water observation cell so as to identify the particles in the flowing water included in the filtrate water, wherein the filtrate water observation cell has an observation bath through which flow of the filtrate water is observed in the flow channel, and a plurality of observation baths are arranged in series along the flow channel.

(9) The filtrate water monitoring apparatus according to the above (7) or (8) may be provided, wherein a porous plate with pores is disposed so as to block the flow channel in the observation bath.

(10) The filtrate water monitoring apparatus according to the above (7) or (8) may be provided, wherein the observation bath has a step to decrease a cross-sectional area of the flow channel along the flow channel.

(11) The filtrate water monitoring apparatus according to any one of the above (7) to (10) may be provided, wherein a plurality of observation baths are arranged and connected in series, and the cross-sectional area of the flow channel, which is made smaller by sizes of the pores or the step, become gradually smaller along the flow of the filtrate water.

(12) The filtrate water monitoring apparatus according to any one of the above (7) to (11) may be provided, wherein the image detection means is provided in a movable way so as to be capable of shooting an image in the filtrate water flowing in any one of the plurality of observation baths.

(13) The filtrate water monitoring apparatus according to any one of the above (10) to (12) may be provided, wherein the step is provided in a V-shape as viewed in a plan view so as to be capable of separating or observing the particles in the flowing water based on difference in density of the particles in the flowing water in the filtrate water observation cell.

(14) A filtrate water monitoring system comprising: a plurality of membrane filtration water-purifying apparatuses and a filtrate water monitoring apparatus that monitors filtrate water filtrated through each of the membrane filtration water-purifying apparatuses may be provided. The filtrate water monitoring system further comprises: filtrate water pipe line systems connected respectively to outlets of the plurality of membrane filtration water-purifying apparatuses; branch filtrate water pipe line systems respectively connected to the filtrate water pipe line systems, the branch filtrate water pipe line systems sampling part of the filtrate water as sample water from the filtrate water pipe line systems; a filtrate water observation cell connected to a midpoint of at least one pipe line system in the branch filtrate water pipe line systems, and the filtrate water observation cell having a flow channel in which the filtrate water flows; and image detection means for shooting an image in filtrate water flowing in the flow channel of the filtrate water observation cell, and for identifying particles in the flowing water included in the filtrate water, wherein the filtrate water observation cell has an observation bath through which flow of the filtrate water is observed in the flow channel, and a plurality of filtrate water observation cells are arranged in series along the branch filtrate water pipe line system.

(15) A filtrate water monitoring system comprising: a plurality of membrane filtration water-purifying apparatuses and a filtrate water monitoring apparatus that monitors filtrate water filtrated through each of the membrane filtration water-purifying apparatuses may be provided. The filtrate water monitoring system comprises: filtrate water pipe line systems connected respectively to outlets of the plurality of membrane filtration water-purifying apparatuses; branch filtrate water pipe line systems respectively connected to the filtrate water pipe line systems, the branch filtrate water pipe line systems sampling part of the filtrate water as sample water from the filtrate water pipe line systems; a filtrate water observation cell connected to a midpoint of at least one pipe line system in the branch filtrate water pipe line systems, and the filtrate water observation cell having a flow channel in which the filtrate water flows; and image detection means for shooting an image in filtrate water flowing in the flow channel of the filtrate water observation cell, and for identifying particles in the flowing water included in the filtrate water, wherein the filtrate water observation cell has an observation bath through which flow of the filtrate water is observed in the flow channel, and a plurality of filtrate water observation baths are arranged in series along the flow channel.

(16) A filtrate water monitoring system comprising: a plurality of membrane filtration water-purifying apparatuses and a filtrate water monitoring apparatus which monitors filtrate water filtrated through each of the membrane filtration water-purifying apparatuses may be provided. The filtrate water monitoring system further comprises: filtrate water pipe line systems respectively connected to respective outlets of the plurality of membrane filtration water-purifying apparatuses; branch filtrate water pipe line systems respectively connected to the filtrate water pipe line systems, the branch filtrate water pipe line systems sampling part of the filtrate water as sample water from the filtrate water pipe line systems, physical detection means for utilizing or detecting a physical phenomenon which varies depending on behavior of particles in flowing water flowing in the branch filtrate water pipe line systems, the physical detection means connected to at least one pipe line system in the branch filtrate water pipe line systems; a filtrate water observation cell which is arranged downstream of the physical detection means and in the branch filtrate water pipe line system and which has inside a flow channel in which the filtrate water flows, and image detection means for shooting an image in the filtrate water flowing in the flow channel of the filtrate water observation cell, and for identifying impurities included in the filtrate water.

EFFECT OF THE INVENTION

In accordance with the present invention, for example, when particle weight in the flow channel exceeds a given value and a value of the turbidity meter exceeds a predetermined value, the particle measurement utilizing an image may be started such that it is not necessary to perform image measurement all the time. Generally, a turbidity meter is to measure an absolute value of macro particle amount in the flow channel in which the flow rate is relatively high, and image measurement in the flow channel in the observation plate of the observation cell is to measure a state of individual particles at the micro level. Accordingly, because it is not necessarily efficient to perform measurement of all the water samples taken from the membrane filtration water-purifying apparatus by the image measurement serving as micro measurement means, macro measurement means can be complemented with this. Macro particle measurement is capable of capturing partially existing particles that are present unevenly in the flow channel depending on the way of setting a preset value. On the other hand, in the micro particle measurement, a portion of the sampled water in which no particles exist may be measured depending on the way of sampling. In such a case, it is determined whether or not there are particles by the macro particle measurement. Thereafter, the water is concentrated so as to increase the ratio of those particles accounted in the sampled water, which enables the micro measurement to measure particles even in the partially sampled water. By performing the micro particle measurement even for an extremely small amount of flowing water, it is possible to stably perform the image measurement even in a case where particles are dispersed unevenly or the amount of particles is extremely low in the flowing water.

Further, when the filtration film is ruptured, broken pieces of the filtration film which are generated and/or objects supposed to be removed by filtration (those which the unbroken original filtration film traps) flow out so as to be included as impurities in the flow channel of the filtrate water pipe line system. Some of those are trapped and accumulated at a dam of the observation bath of the observation cell inside the branch filtrate water pipe line system, which can be detected and analyzed to be identified through an image detection by a camera. However, it is difficult to identify only the broken pieces in the case where other objects than the broken pieces exist in the flow channel at the same time. It becomes easier to specify the broken pieces if the broken pieces and the other impurities can be respectively separated and observed in the observation baths of a plurality of corresponding observation cells.

As differences between the broken pieces and the other impurities, dimensions (sizes), densities, shapes, and the like of the objects are named. And, the sizes of impurities to be trapped are considered to be substantially determined depending on the size of a dam (step) provided in the observation bath of the observation cell. By utilizing this characteristic, detection through an image is made easier by providing the dam (step) in a size comparable to the sizes of the impurities to be trapped.

Further, provided that an observation bath of the observation cell having a dam (step) which is capable of trapping impurities in other sizes than broken pieces of the film is provided upstream, and an observation bath having a dam (step) which is capable of trapping impurities such as broken pieces is provided downstream, the other impurities than the broken pieces are eliminated upstream, and the flowing water including only the broken pieces pass through the inside of the observation bath downstream, which makes it possible to more precisely detect an image of the broken pieces.

Generally, the size of target broken pieces is 2 μm which is the smallest among those of impurities, and it is possible to achieve the above-described object by providing observation baths having dams (steps) (for example, 10 μm and 20 μm) that trap impurities in sizes greater than the smallest size upstream thereof.

Further, in the case where sizes of broken pieces differ depending on the types thereof, the broken pieces may be sorted out by the size as a plurality of dams (steps) having different sizes are provided, thereby enabling the measurement to detect images according to individual sizes.

Moreover, in the case where different types of broken pieces have different densities, the observation baths may be arranged such that an upper-stream observation bath has a dam (step) capable of trapping impurities of higher density, thereby enabling the image detection to be performed more efficiently.

In addition to the broken pieces, particles to be originally removed by filtering, i.e., particles of an abnormally large size passing through the broken portion of the filter can be sorted out. Further, the sorting-out may be performed by the dam (step) of the filtrate water monitoring plate as well as by porous plates and the like. Accordingly, any means capable of performing image observation and filtering can be included.

BRIEF DESCRIPTION OF THE DRAWINGS

FIG. 4 shows configuration samples of observation baths of filtrate water observation plates of the filtrate water monitoring apparatus.

FIG. 12 is a view showing schematically another filtrate water monitoring apparatus according to Embodiment 5.

DESCRIPTION OF NUMERALS 1. filtrate water monitoring apparatus,
2. sampling filtrate and image shooting part,
3. image analysis part (image analysis means),
4a. outgoing pipe, 4b. return pipe,
5. flow rate meter, 6. first three-way connector,
7. needle valve, 8. second three-way connector,
9. deforming device,
10. filtrate water observation plate, 11, 12. pump,
13, 14. gate valve, 15. inlet side connector,
16. observation bath, 17. collection bath,
18. outlet side connector, 19. impurity (microorganism)
20. optical device (image shooting means),
21. objective lens, 22. digital camera, 23. step,
24. porous plate,
30. membrane filtration water-purifying apparatus,
31. water supply pipe line system,
32. branch filtrate water pipe line system,
32a, 32b. flange, 33. orifice flange,
33a. straight pipe part, 33b, 33c. flange part,
34. orifice,
40. membrane filtration water-purifying system,
102. glass plate, 104. resin plate, 110. abyss part,
110a, 110b, 110c, 110d. observation bath,
116 bead particle, 130. bypass pipe,
160. turbidity meter, 160a. fine-particle counter,
210. self-cleaning mechanism

BEST MODE FOR CARRYING OUT THE INVENTION

Hereinafter, an embodiment of the present invention will be described in detail with reference to the drawings.

Embodiment 1

A filtrate water monitoring apparatus of Embodiment 1 is used for detecting damage to a filtration film (a filtration medium) set in the membrane filtration water-purifying apparatus to monitor its performance degradation (caused by damage or its lifetime) in order to ensure the safety of filtrate water discharged from a membrane filtration water-purifying apparatus used for purifying any type of water source including natural water such as river water, lake water, or groundwater. This filtration film may be, for example, a hollow-fiber membrane module. However, the filtration film is not limited to the hollow-fiber membrane module.

Figure 1:
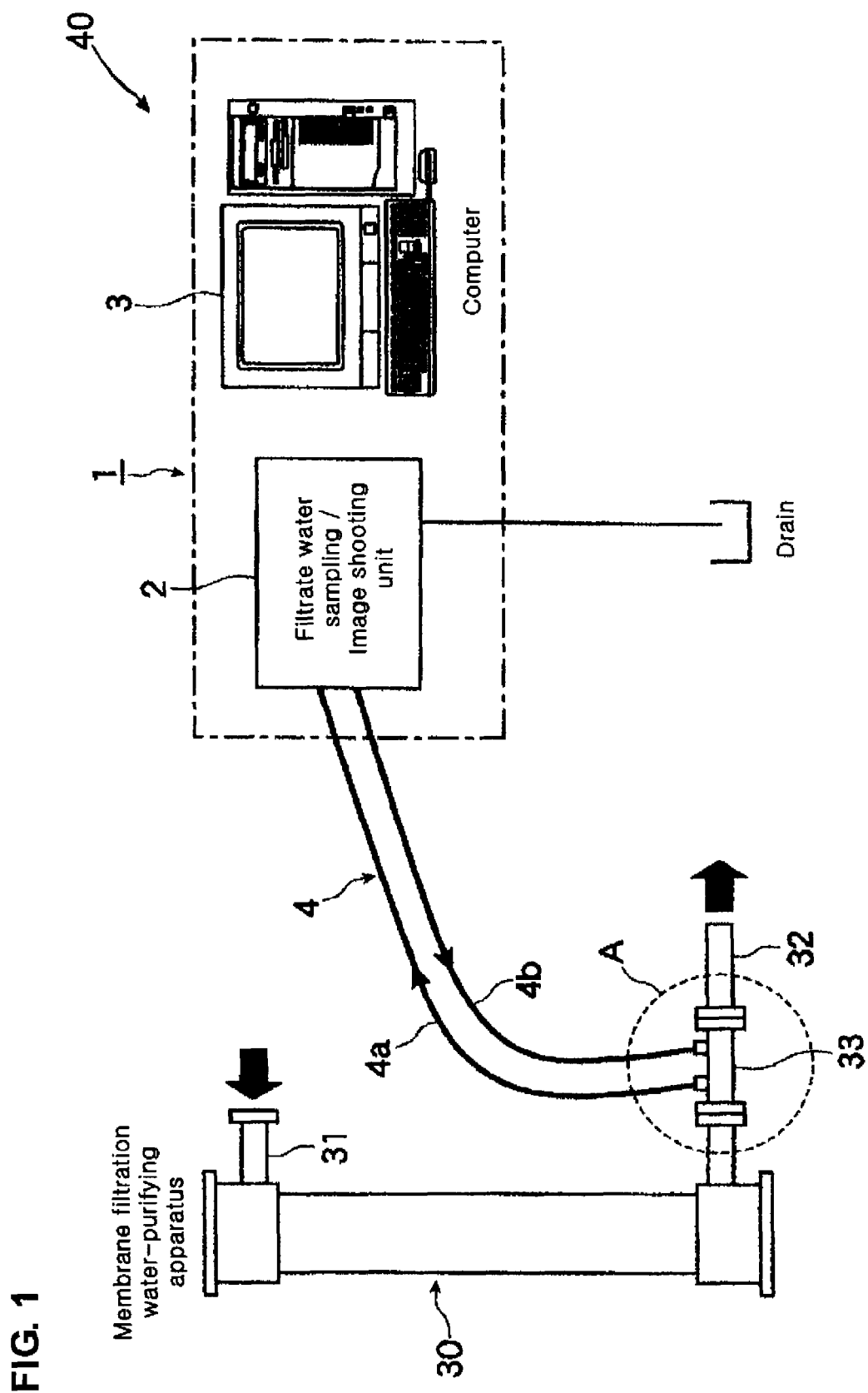
FIG. 1 shows a general configuration of a filtrate water monitoring apparatus and a membrane filtration water-purifying apparatus according to Embodiment 1.

As shown in FIG. 1, a filtrate water monitoring apparatus 1 includes a filtrate water sampling/image shooting unit 2 and an image analysis unit 3 that analyzes an image of filtrate water obtained by the filtrate water sampling/image shooting unit 2 to identify impurities included in the filtrate water. The filtrate water sampling/image shooting unit 2 is set along the way of a branch filtrate water pipe line system 4. The branch filtrate water pipe line system 4 is made to branch from a filtrate water pipe line system connected to an outlet of a membrane filtration water-purifying apparatus 30 in order to take sample water. A water supply pipe line system 31 is a pipe line to supply unclean water (water to be filtrated) to the membrane filtration water-purifying apparatus 30. The filtrate water pipe line system 32 is a pipe line to supply purified water (filtrate water) obtained by the membrane filtration water-purifying apparatus 30 to a reservoir/utilization area. Here, impurities may mean objects to be filtrated which cannot be removed by the membrane filtration water-purifying apparatus 30, broken pieces of the filtration film, and the like. Further, the impurities may be treated as a generic name for substances which are not the targeted objects, and generally, inorganic substances such as dust and sand, organic substances such as broken pieces of vegetation, broken pieces of animals and plants like bone fragments, biotic metabolite, and dead or alive microorganisms, may be included.

Figure 2:
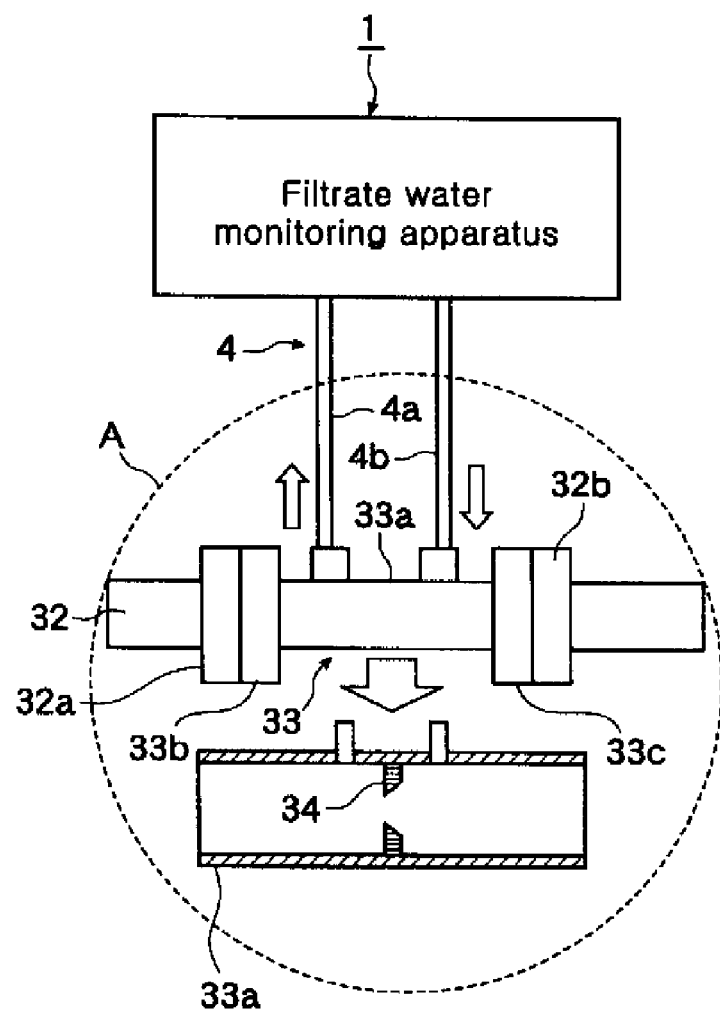
FIG. 2 is an enlarged part view of A part of FIG. 1, which has an additional cross sectional view.

The branch filtrate water pipe line system 4 is made to branch from the filtrate water pipe line system as follows. That is, as shown in FIG. 2 in an enlarged manner, a part of the pipe near the connected portion of the filtrate water pipe line system 32 to the membrane filtration water-purifying apparatus 30 is cut off, and an orifice flange 33 is instead inserted therein to be connected and coupled in a liquid-tight manner. The orifice flange 33 is built into the filtrate water pipe line system 32 such that flange parts 33b and 33c are integrally provided at both ends of a short straight pipe part 33a, and these flange parts 33b and 33c are coupled with flanges 32a and 32b respectively formed integrally at the opposing ends of the filtrate water pipe line system 32 to the both ends of the cut-off part by means of fastening means such as bolts.

An orifice 34 is provided inside the straight pipe part 33a, and a difference in pressure is generated in a fluid (filtrate water) flowing inside the filtrate water pipe line system 32 before and after the orifice 34. Then, an inlet end to an outgoing pipe 4a of the branch filtrate water pipe line system 4 is connected to the high-pressure side upstream of the orifice 34, and an outlet end from a returning pipe 4b of the branch filtrate water pipe line system 4 is connected to the low-pressure side downstream. An outlet end of the outgoing pipe 4a and an inlet end of the returning pipe 4b are connected to the filtrate water sampling/image shooting unit 2. The filtrate water on the high-pressure side upstream of the orifice 34 is guided to the filtrate water sampling/image shooting unit 2 through the outgoing pipe 4a, and filtrate water which is excess there is returned to the low-pressure side downstream of the orifice 34 through the returning pipe 4b. In this way, the filtrate water sampling/image shooting unit 2 in Embodiment 1 can be conveniently incorporated and established into the existing membrane filtration water-purifying apparatus 30 only by connecting the orifice flange 33 of the branch filtrate water pipe line system 4 in a liquid tight manner to the cut-off part of the filtrate water pipe line system 32. In addition, a throttle nozzle may be utilized instead of the orifice 34. The water supply pipe line system 31 for natural water is connected to the inlet of the membrane filtration water-purifying apparatus 30.

A filtrate water monitoring system 40 is constituted of the water supply pipe line system 31, the membrane filtration water-purifying apparatus 30, the filtrate water pipe line system 32, the orifice flange 33, the branch filtrate water pipe line system 4, and the filtrate water monitoring apparatus 1. A membrane filtration water-purifying system is constituted of the water supply pipe line system 31, the membrane filtration water-purifying apparatus 30, the filtrate water pipe line system 32, the orifice flange 33, and the branch filtrate water pipe line system 4, and the membrane filtration water-purifying system may be singular or plural. In a case in which there are a plurality of membrane filtration water-purifying systems, a plurality of the branch filtrate water pipe line systems 4 and a plurality of the filtrate water sampling/image shooting units 2 of the filtrate water monitoring apparatus 1 may be respectively connected thereto, and valves may be provided to the respective connection parts, to switch the membrane filtration water-purifying apparatus 30 that performs monitoring of filtrate water. Further, in a case in which there are a plurality of membrane filtration water-purifying systems, the filtrate water monitoring apparatuses 1 which are the same number of the membrane filtration water-purifying systems may be prepared, and the filtrate water monitoring apparatuses 1 may be respectively connected to the respective branch filtrate water pipe line systems 4.

Figure 3:
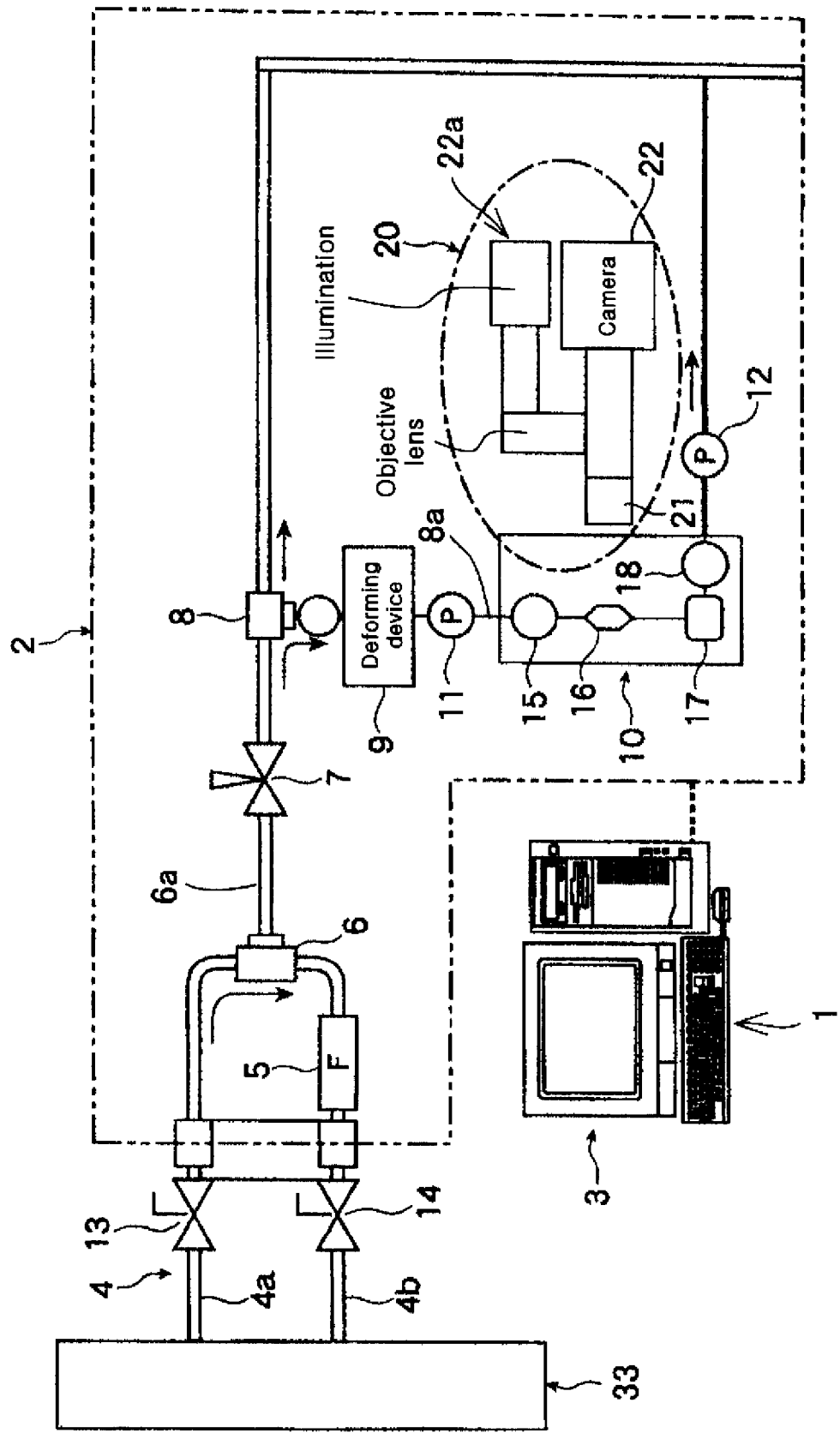
FIG. 3 shows a general configuration of the filtrate water monitoring apparatus.

FIG. 3 shows a detailed configuration of the filtrate water monitoring apparatus 1 in Embodiment 1. Some of the filtrate water is taken as a sample water upstream of the orifice flange 33, and the filtrate water is guided to the filtrate water sampling/image shooting unit 2 of the filtrate water monitoring apparatus 1 through the outgoing pipe 4a of the branch filtrate water pipe line system 4. The filtrate water sampling/image shooting unit 2 is constituted of mainly a filtrate water observation plate 10 and an optical device 20. In the filtrate water sampling/image shooting unit 2, a required quantity of sample water is made to branch by a first three-direction connector 6 to be guided to a second three-direction connector 8 through a pipe line 6a and a needle valve 7. The sample water is further made to branch through the second three-direction connector 8 to be guided to the filtrate water observation plate (filtrate water observation cell) 10 provided in the middle of the pipe line 8a through a pipe line 8a. Pumps 11 and 12 are respectively set on the pipe lines as the pipe line 8a at the inlet side and the outlet side of the filtrate water observation plate 10. Since the pump 11 only has to take care of a pressure loss caused by flowing of filtrate water up to the pump 11 and a pressure loss caused by flowing of filtrate water from the pump 11 up to the pump 12, a required output power by the pump 11 may be relatively small, and a pressure increase in the filtrate water inside the filtrate water observation plate 10 is suppressed to be low, thereby avoiding unbearable pressure inside the filtrate water observation plate 10. This is especially advantageous for a case where the filtrate water observation plate 10 is formed by bonding two glass plates. Here, only one filtrate water observation plate 10 is explained by way of example. However, two or more filtrate water observation plates 10 may be connected in series along the branch filtrate water pipe line system 4, and a filtrate water observation cell is constituted of one or more filtrate water observation plates 10.

Excess filtrate water (unused sample water) which does not flow in a direction of the filtrate water observation plate 10 through the first three-direction connector 6, i.e., in a direction of the pipe line 6a is returned to the low pressure side downstream of the orifice 34 of the orifice flange 33 through the returning pipe 4b. A flow rate of the excess filtrate water is measured by a flow meter 5 disposed at an upstream part of the returning pipe 4b, and apertures of cutoff valves 13 and 14 respectively provided in the middle of the outgoing pipe 4a and in the middle of the returning pipe 4b are appropriately adjusted in accordance with a flow rate to be measured. The filtrate water discharged from the pump 12 and the excess filtrate water which does not flow in the direction of the filtrate water observation plate 10 through the second three-direction connector 8, i.e., in the direction of the pipe line 8a flow into each other to be wasted as drain water. Because new filtrate water always flows through the filtrate water observation plate 10 in this way, it is possible to always grasp a current situation of the filtration film of the membrane filtration water-purifying apparatus 30.

A deforming device 9 is provided upstream of the filtrate water observation plate 10 in the pipe line 8a. The deforming device 9 is a device to remove bubbles included in filtrate water. Thus, since the filtrate water flowing inside an observation bath 16 of the filtrate water observation plate 10 does not include foam, image shooting of impurities included in the filtrate water, which shows a result of a damage to the filtration film, and identifying the impurities are more precisely conducted such that it is possible to grasp the situation of the damage to the filtration film more accurately.

Figure 17:
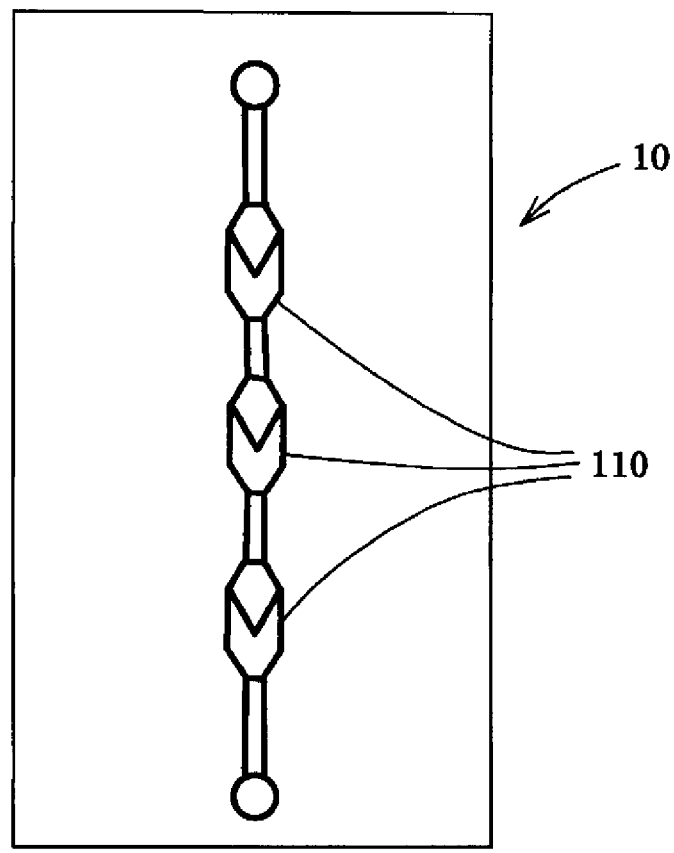
FIG. 17 is a view showing schematically a plurality of observation baths of another embodiment.

The filtrate water observation plate 10 is formed by bonding two plates which are formed of any one of materials of glass, resin, and metal, and whose surfaces are coated with a hydrophilic membrane coating (refer to FIGS. 5 and 6), and a flow channel constituted of an inlet side connector 15, the observation bath 16 (a collection bath 17), and an outlet side connector 18 is formed in the joining area. Then, when the filtrate water flows in the observation bath 16, an image of the filtrate water is taken by the optical device (image shooting means) 20 positioned adjacent thereto. Impurities including objects to be removed by filtrating (foreign substances such as fine stones and splinters of wood, microorganisms such as bacteria and coli bacteria) that damage the filtration film are captured in the image. These impurities are collectively shown by reference numerals 19 in FIG. 4. The image analysis unit (image analysis means) 3 receiving image information output from the optical device 20 analyzes the image information to identify what substances (impurities) are captured by the image in fact (refer to FIG. 13). The case in which one filtrate water observation plate 10 has only one observation bath 16 in its flow channel is described as an example in FIGS. 5 and 6A to 6D. However, this is not limited to the case. The filtrate water observation plate 10 may have two or more observation baths 16 in series along the flow channel as shown in FIG. 17. In the case where the observation baths 16 are arranged in series, the height of each flow channel in which the filtrate water is directed from upstream to downstream is made narrower by each step and the height of each flow channel may be lowered step by step from upstream to downstream.

In the optical device 20, a digital camera 22 shoots an image in the filtrate water to be observed through an objective lens 21, and the digital camera 22 transmits the image information taken as an image to the image analysis unit 3. The digital camera 22 has an illumination 22a that illuminates an object to be observed. The image analysis unit 3 is constituted of mainly a computer. When the computer receives the image information output from the optical device 20, the image analysis unit 3 identifies shapes, sizes, and the number of impurities in the image information by image processing, and compares those with an image pattern stored in its storage unit to analyze and identify what the impurities included in the filtrate water are. Because the work for analyzing/identifying impurities by the computer is performed while the image thereof is displayed and enlarged on the display of the computer, it is possible for a human to confirm the identification work. Further, by networking the optical device 20 and the computer, it is possible to perform the work for analyzing/identifying the impurities even at a point distant from the optical device 20, which makes it possible to remotely monitor filtrate water. The impurities included in the filtrate water are identified and the number of the impurities are grasped in this way such that it is possible to confirm the situation of damage to the filtration film installed inside the membrane filtration water-purifying apparatus 30.

The observation bath 16 and the collection bath 17 of the filtrate water observation plate 10 are enlarged parts of the flow channel for filtrate water (sample water). In particular, the observation bath 16 may be configured so as to, not only make filtrate water flow in the enlarged flow channel (refer to FIG. 4A), but also be as follows in order to make it easy to shoot an image in the filtrate water by the optical device 20 and capture the impurities in the image. For example, as shown in FIG. 4B, a step 23 that blocks impurities may be provided in the enlarged flow channel. As shown in FIG. 4C, a porous plate 24 having pores for the passage of filtrate water may be provided so as to cover the enlarged flow channel in the enlarged flow channel. In this way, only impurities included in the filtrate water can be blocked and removed by filtering with the porous plate 24 without interrupting the flow of filtrate water flowing in the observation bath 16, thereby enabling capturing only the impurities and shooting reliably images of the impurities. The collection bath 17 is a portion serving as a header for communicating with the outlet sides of the observation baths 16 of the respective filtrate water observation plates 10 in the case where a plurality of filtrate water observation plates 10 are integrated to constitute one filtrate water observation cell.

The filtrate water monitoring apparatus 1 in Embodiment 1 is configured as described above such that the apparatus 1 is capable of achieving the following advantageous effects. Provided that the filtrate water pipe line system 32 connected to the outlet of the membrane filtration water-purifying apparatus 30 and the branch filtrate water pipe line system 4 are opened for hours (in this case, the water supply pipe line system 31 connected to the inlet of the membrane filtration water-purifying apparatus 30 is also opened), and that the optical device (image shooting means) 20 and the image analysis unit (image analysis means) 3 are kept operating for 24 hours, monitoring of filtrate water discharged from the membrane filtration water-purifying apparatus 30 can be performed in real time for 24 hours by the image analysis without stopping the operation of the membrane filtration water-purifying apparatus 30. Moreover, it becomes possible to perform remote monitoring of the filtrate water through the network of the computer serving as the image analysis means, and it is rather easy to adjust observation and measurement devices since they are composed only of the filtrate water observation plate 10, the optical device 20, and the image analysis unit 3. Further, it also becomes possible to manage the traceability (history) of the filtrate water by accumulating data of the received information and the results of analysis thereof in the image analysis unit 3. In accordance therewith, the easiness of the operation and the reliability of the monitoring of the performance degradation and the damage detection of the filtration film in the membrane filtration water-purifying apparatus 30 can be improved, thereby enabling further ensuring the safety of the filtrate water produced by and discharged from the membrane filtration water-purifying apparatus 30.

Further, since the deforming device 9 is provided upstream of the filtrate water observation plate 10, the filtrate water flowing in the observation bath 16 of the filtrate water observation plate 10 does not include foam such that it becomes possible to grasp more precisely the situation of the damaged filtration film by performing more accurately image capture and identification of the impurities (microorganisms and the like) included in the filtrate water, which show results of damage of the filtration film. Thus, the reliability of the damage detection and the performance degradation monitoring of the filtration film in the membrane filtration water-purifying apparatus 30 can be further improved.

Further, in the case where the step 23 that blocks the impurities or the porous plate 24 having pores for filtrating filtrate water is provided in the observation bath 16 of the filtrate water observation plate 10, only the impurities included in the filtrate water can be blocked or retained by filtering so as to be captured without interrupting the flow of filtrate water flowing in the observation bath 16, thereby enabling shooting reliably images thereof. Thus, the reliability of the performance degradation monitoring and the damage detection of the filtration film in the membrane filtration water-purifying apparatus 30 can be further improved.

Moreover, since the filtrate water monitoring apparatus 1 can be coupled with and incorporated into the existing membrane filtration water-purifying apparatus 30 only by connecting the orifice flange 33 to the cut-off part of the filtrate water pipe line system connected to the outlet of the membrane filtration water-purifying apparatus 30, it is extremely easy to put them together and install the apparatus 1 therein.

Figure 5:
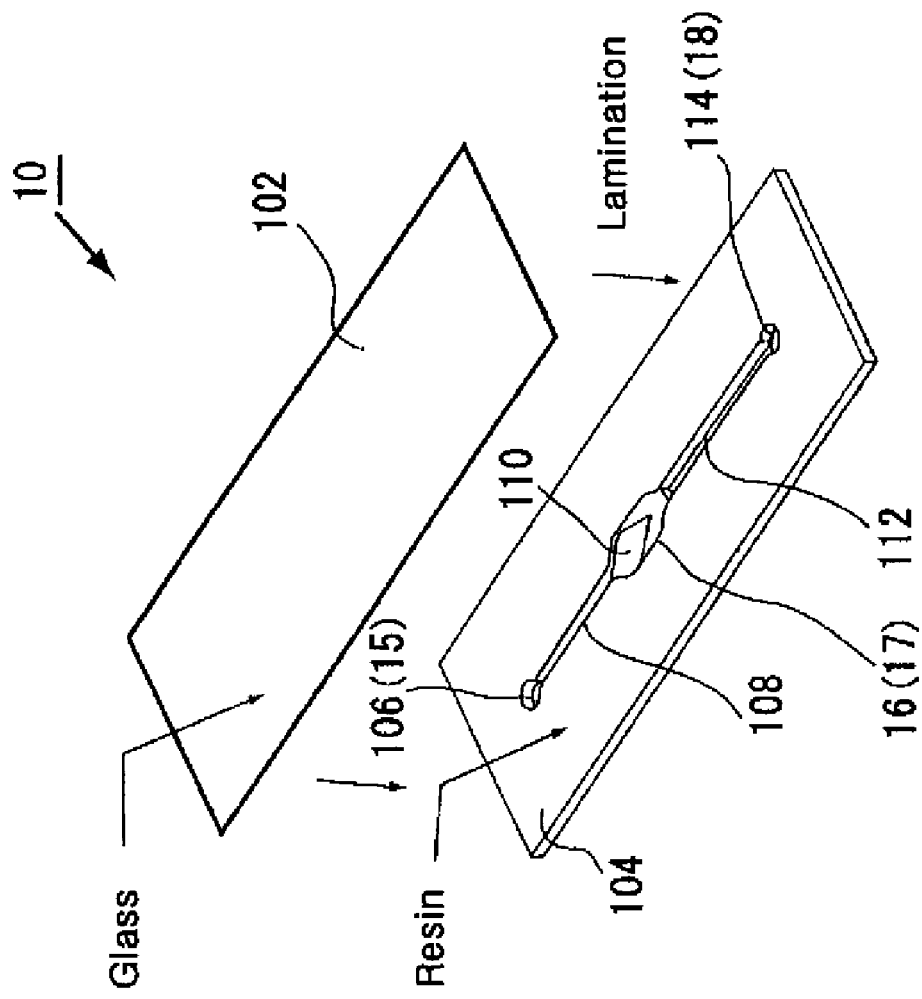
FIG. 5 is an exploded view of a filtrate water observation plate.
Figure 6A:
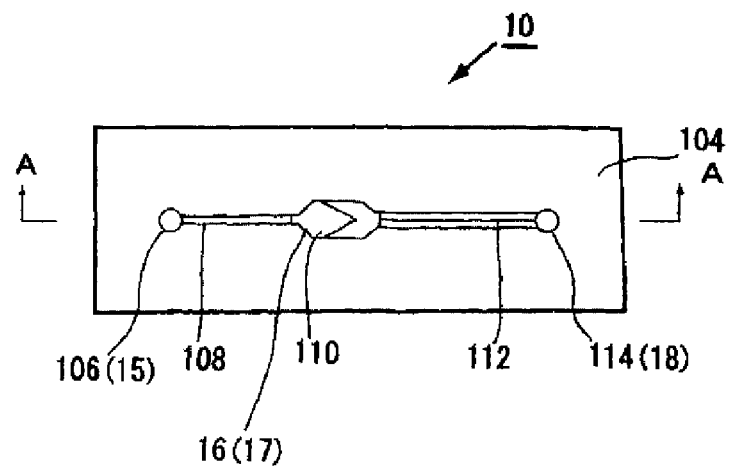
FIGS. 6A to 6D show details of configuration elements of a filtrate water observation plate.
Figure 6B:
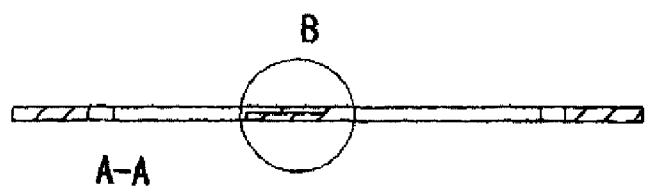
Figure 6C:
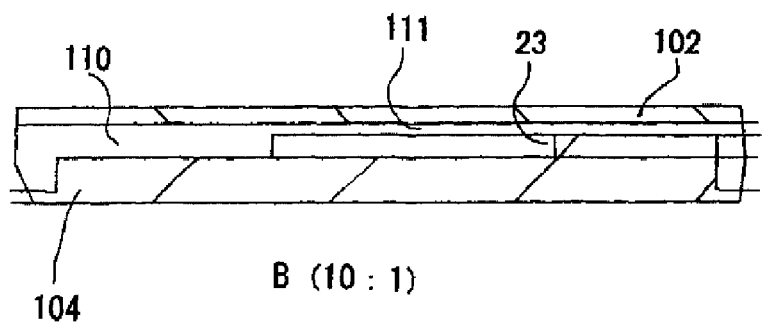
Figure 6D:
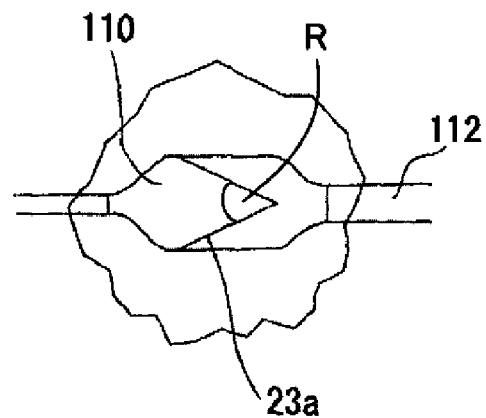

FIG. 5 is an exploded perspective view of the filtrate water observation plate 10. The filtrate water observation plate 10 is constituted mainly of a transparent glass plate 102 and a plate 104 made of resin, in which a concave portion forming the observation bath 16 or the like is made (scraped), as the glass plate 102 and the plate 104 are glued together as shown by arrows. Through holes 106 and 114 are provided at both ends of the concave portion forming a groove extending in the substantially center of the plate width in the longitudinal direction of the resin plate 104, and the filtrate water observation plate 10 is configured so as to guide the filtrate water from the outside to the observation bath 16 to discharge the filtrate water to the outside. The groove 108 having the through hole 106 at the one end guides the filtrate water introduced from the through hole 106 to an abyss part 110 upstream of the observation bath 16 at the other end of the groove 108. The filtrate water flowing over the step 23 flows into the shallow part downstream from the step 23 (refer to FIG. 6) and passes through the groove 112, and then is discharged outside of the system via the through hole 114.

The impurities in the filtrate water easily pool on the abyss side of the step 23 in the observation bath 16, and their planar shapes can be observed via the upper glass plate 102 (FIGS. 6A to 6D). The step 23 is different from the step 23 as shown in FIG. 4B such that the step 23 of FIGS. 6A to 6D is formed into a V-shape in the plan view so as not to dam the flow of the filtrate water, but to let the flow pass through the step 23 partially as the impurities are easily collected in a valley bottom of the V-shape. It is considered that this occurs because water flows along a wall 23a of the step 23 and the flow rate of the filtrate water is accelerated at the valley bottom of the V-shape serving as the final outlet, from which the water flows out. Further, in particular, in the case where a depth of the abyss part 110 is much deeper than a depth on the shallow water side, a flow of water easily stagnates in the lower corner portion of the step 23 (a boundary area between the abyss part 110 and the step 23), and a high-density of impurities easily settle down to gather in the lower corner portion. Therefore, even if the impurity concentration is originally low, the number of impurities gathering in the lower corner portion gradually increases as time goes by, thereby making it easier to confirm the shapes of the impurities by observation via the glass plate 102.

A widen angle R of the V-shape of the step 23 is approximately 50 degrees in this embodiment. This angle can be appropriately changed in accordance with types, concentrations, measurement accuracies, and measurement conditions of impurities to be accumulated. However, generally, the angle is preferably an acute angle. The height of the step 23 and the depth of the abyss part 110 will be hereafter described in more detail with reference to FIGS. 7A to 7D.

FIGS. 7A to 7D show photographs of an assemble of the filtrate water observation plate 10, show schematically a state in which bead particles 116 assuming as the impurities are gradually gathering in the filtrate water observation plate 10 by the step 23 and the wall 23a thereof, and show schematically abyss parts 110 of 20 μm and 10 μm, respectively, in the filtrate water observation plates 10.

Figure 7A:
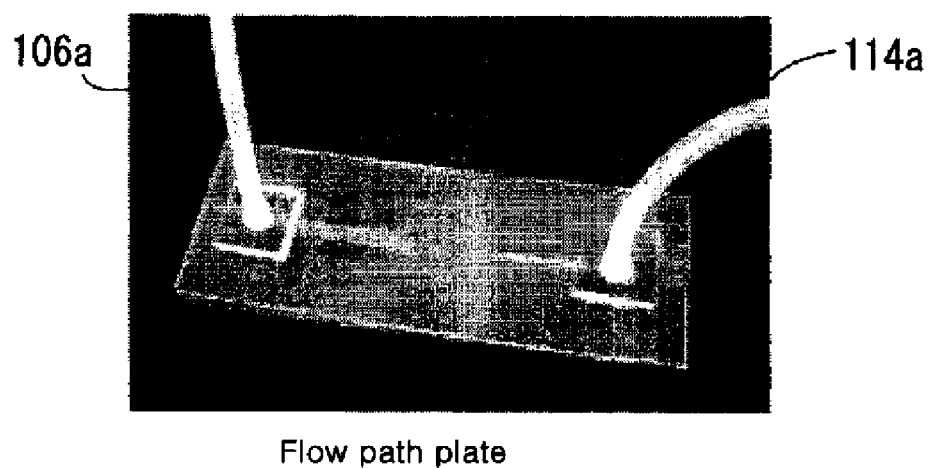
FIG. 7A shows a picture of an assembled filtrate water observation plate.
Figure 7B:
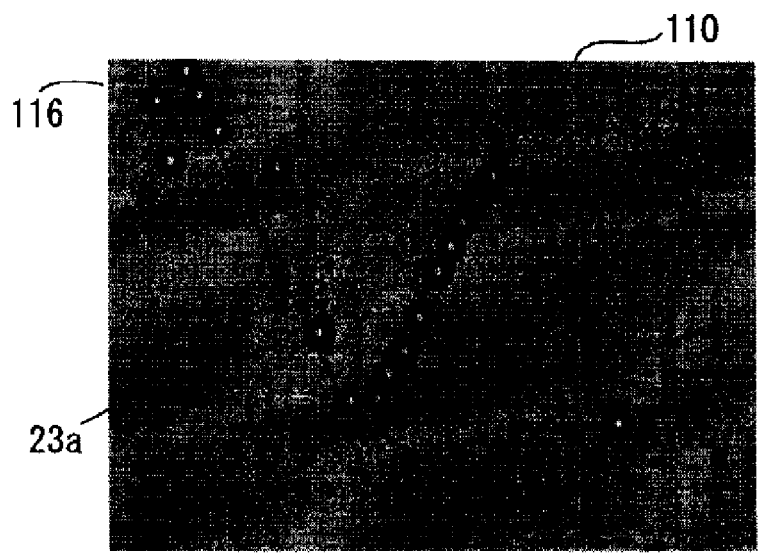
FIG. 7B shows an evaluation result with bead particles.
Figure 7C:
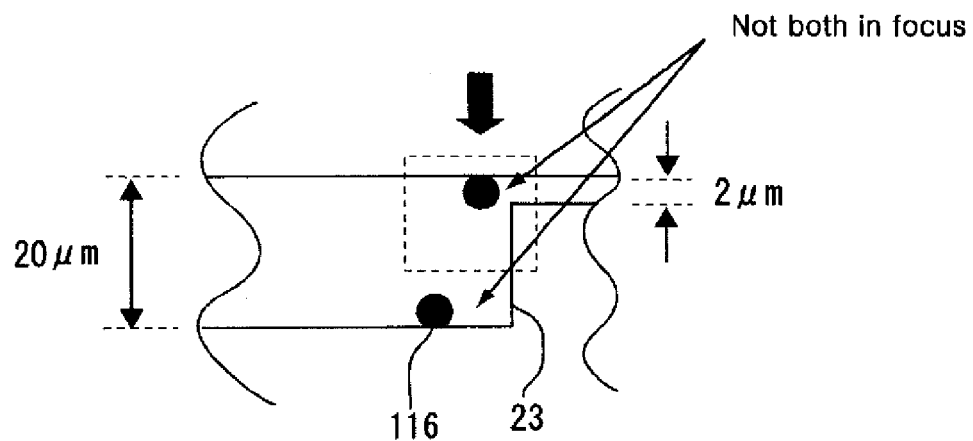
FIG. 7C is a schematic diagram of a step in the observation bath.
Figure 7D:
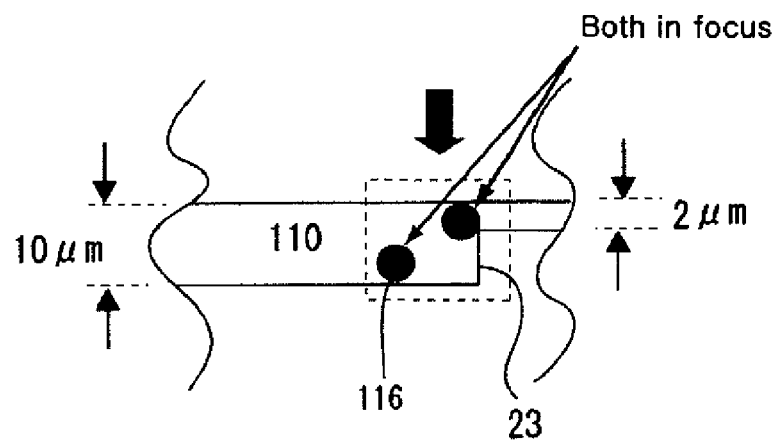
FIG. 7D is a schematic diagram of another step in the observation bath other than that of FIG. 7C.

The diameters of the bead particles 116 are greater than a depth of 2 μm on the shallow part side 111 of the step 23, and the bead particles 116 are incapable of flowing out of the shallow part side 111, and are remaining in the abyss part 110 in front of the step 23. In this way, the size of the minimum particle (for example, a diameter in the spherical approximation) which can be trapped is determined in accordance with a depth of the shallow part side. On the other hand, the size of the maximum particle (for example, a diameter in the spherical approximation) which can be observed is determined in accordance with the depth of the abyss part 110. Accordingly, a range of sizes of particles introduced into and retained in the abyss part 110 serving as the observation bath is characterized by these depths. In the case where a specific gravity of the bead particles 116 retained in the abyss part 110 is greater than 1, the bead particles 116 tend to sink to remain in the bottom portion of the abyss part 110. In the case where a depth of the abyss part 110 is 20 μm as shown in FIG. 7C, the bead particles 116 floating above the step 23 flow to the shallow part side due to momentum of the flow of water and the bead particles 116 sinking to the bottom of the abyss part 110 are distanced by 20 μm to the maximum. Therefore, unless the depth of field of the optical device 20 is sufficient, it is impossible to simultaneously focus on the both bead particles 116. On the other hand, when a depth of the abyss part 110 is 10 μm as shown in FIG. 7D, the maximum distance between the floating bead particles 116 and the sunk bead particles 116 is 10 μm, thereby making it easier to simultaneously focus on the both bead particles 116. In particular, in the case where a magnification of the optical device 20 is high, a depth of field tends to be small, thereby making the effect more prominent. That is, provided that the depth of the abyss part 110 is adjusted in a preferable range, it is possible to screen the particles of sizes to be measured and obtain measured images thereof in focus. Moreover, it is possible to make the particles characterized by the range of favorable sizes for the measurement as the depth of the shallow part side 111 is relatively adjusted.

Figure 8:
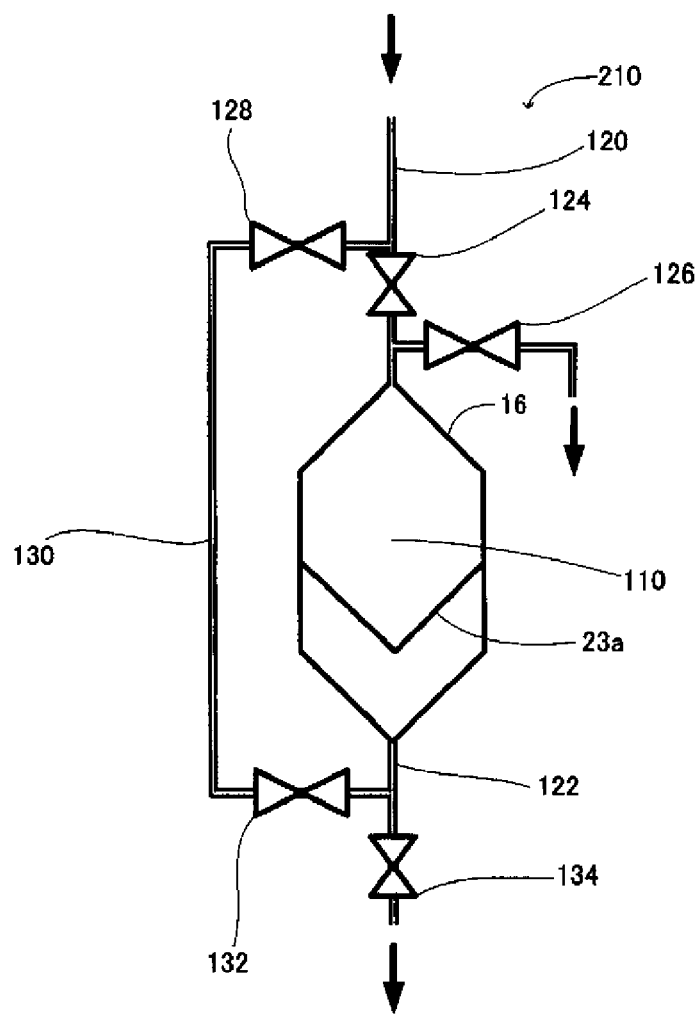
FIG. 8 is a schematic diagram of a self-cleaning mechanism of a filtrate water observation plate.

FIG. 8 is a schematic diagram for explanation of a self-cleaning mechanism 210 for the observation bath 16 and the like of the filtrate water observation plate 10, that can be applied to Embodiment 1. The filtrate water flows in a pipe 120 in a direction of the arrow in the upper side of the drawing. A valve 124 is normally open, and the filtrate water directly flows into the abyss part 110 of the observation bath 16. At that time, a valve 126 toward a branch flow pipe is closed, and the flow is not made to branch. The water flowing into the abyss part 110 flows toward the halfway line along the wall 23a as described above, and flows over the step 23 to flow toward the shallow part side. At this time, the impurities of appropriate sizes are dammed in front of the step 23, and are observed by the optical device 20. The water flowing toward the shallow part side further passes through a distributing water pipe 122, and passes through a valve 134 normally open to be discharged out of the system. At this time, a valve 132 toward the side of a bypass pipe 130 is closed.

In the case where the impurities gather in the observation bath 16 more than necessary or in the case where the state inside the observation bath 16 is once reset, the self-cleaning mechanism 210 can be made to automatically or manually operate. That is, by closing the valve 124 and opening the valve 128, the water flowing in the pipe 120 does not go to the observation bath 16 directly, but flows toward the bypass pipe 130. At this time, the valve 132 is open and the valve 134 is closed, and the filtrate water flowing in the bypass pipe 130 passes through the pipe 122 to flow into the observation bath 16 from the shallow part side. The accumulated impurities are pushed by the flow to flow from the upper pipe backward against the normal flow, and are discharged out of the system via the valve 126 to be opened.

Provided that the valves are operated as described above, it is possible to periodically or always carry out cleaning of the observation bath 16, and to successively and stably perform observation through the filtrate water observation plate 10.

Embodiment 2

Figure 9:
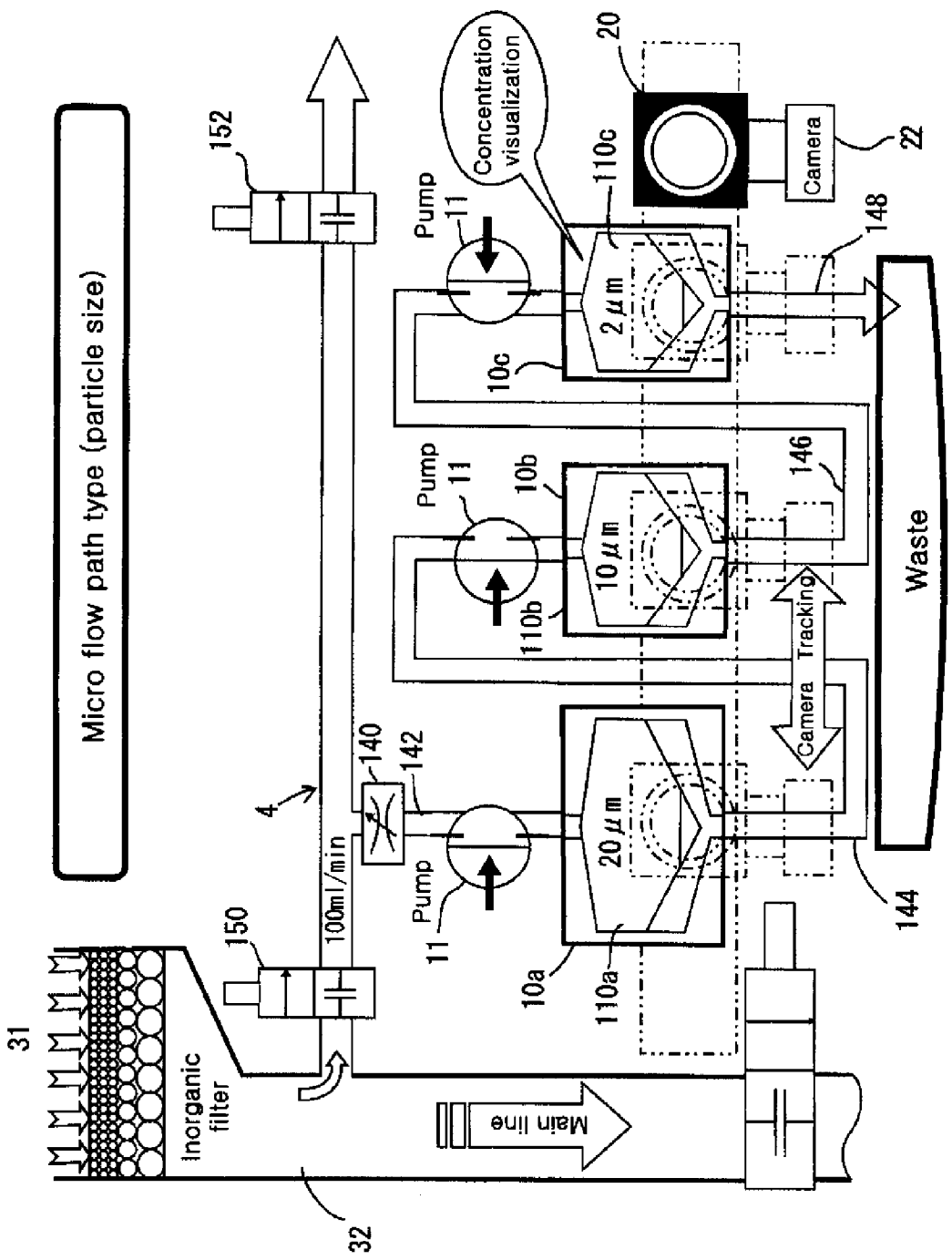
FIG. 9 is a view showing schematically another filtrate water monitoring apparatus according to Embodiment 2.

FIG. 9 is a diagram schematically showing Embodiment 2 of the present invention. Redundant descriptions with Embodiment 1 will be omitted. In the same way as in Embodiment 1, the filtrate water pipe line system 4 is made to branch from a main pipe (main line) through which filtrate water filtrated through the water supply pipe line system 31 passes. A gate valve 150 is set in the filtrate water pipe line system 4, and the gate valve 150 prevents the filtrate water from passing through the filtrate water pipe line system 4 or adjusts a flow amount of filtrate water. Here, a flow rate of approximately 100 ml/min is provided. The filtrate water pipe line system 4 is further made to branch into a branch line 142 having a throttle valve 140, and a gate valve 152 is installed in the main pipe of the filtrate water pipe line system 4, and the filtrate water is directly discharged out of the system when the gate valve 152 is open.

The filtrate water in the pipe 142 made to branch from the filtrate water pipe line system 4 is pressurized so as to compensate for the pressure loss caused so far by the pump 11 and to flow into a filtrate water observation plate 10a. An observation bath 110a is provided in the filtrate water observation plate 10a, and the step 23 (refer to FIG. 7) is provided therein. Impurities of predetermined sizes are blocked and retained in the observation bath 110a by the step 23, and the filtrate water flowing over the step 23 passes through a pipe 144. The filtrate water is further pressurized by the pump 11 to flow into a second filtrate water observation plate 10b. By the step 23 in an observation bath 110b of the filtrate water observation plate 10b as well, impurities in predetermined sizes are retained in the observation bath 110b in the same way, and the filtrate water flowing over the step 23 passes through a pipe 146. The filtrate water is further pressurized by the pump 11 to flow into a third filtrate water observation plate 10c. By the step 23 in an observation bath 110c of the filtrate water observation plate 10c as well, impurities in predetermined sizes are retained in the observation bath 110c in the same way. The filtrate water flowing over the step 23 in the third filtrate water observation plate 10c passes through a pipe 148, to be discharged out of the system. These observation baths 110a, 110b, and 110c are observed for shooting images by the optical device (image shooting means) 20, and are analyzed by the image analysis unit (image analysis means) 3 (refer to FIG. 1). Here, depths of the shallow part sides over the steps 23 in the observation baths 110a, 110b, and 110c are respectively 20 μm, 10 μm, and 2 μm. Accordingly, impurities greater than or equal to 20 μm, 10 μm, and 2 μm can be observed in the respective observation baths 110a, 110b, and 110c. On the other hand, although not shown clearly in the drawing, depths of the abyss sides in the respective observation baths 110a, 110b, and 110c may be respectively adjusted to 50 μm, 20 μm, and 5 μm, and the ranges of particle sizes to be observed can be specified, respectively.

Next, the operations of Embodiment 2 will be described. The sample water in the branched filtrate water pipe line system 4 passes through the throttle valve 140 to flow into the first, second, and third filtrate water observation plates 10a, 10b, and 10c, and an upper-stream filtrate water observation plate among those has a shallow part depth deeper than the step 23. In detail, the depths of the steps/shallow parts in the first, second, and third filtrate water observation plates 10a, 10b, and 10c are respectively 50/20 μm, 20/10 μm, and 5/2 μm, and the sizes of particles to be retained in the observation baths can be limited to a predetermined range by appropriately adjusting the depths of the steps/shallow parts in the filtrate water observation plates. Therefore, greater impurities are remaining in the upper-stream observation bath 110a of the first filtrate water observation plate 10a. Therefore, when the respective observation baths are observed, a magnification of the optical device 20 can be set so as to correspond to the sizes of impurities to be observed, which results in more precise measurement. Further, it is possible to select one of the observation baths 110a, 110b, and 110c to be observed in accordance with the features (sizes, shapes, and the like) of impurities trapped in the respective observation baths 110a, 110b, and 110c, which allows to make the measurement more efficient. Further, in the case where smaller impurities are observed and, for example, in the case where only the third filtrate water observation plate 10c is used, it is possible to cause the filtrate water observation plate 10c to be clogged with larger impurities retained inside the filtrate water observation plate 10c such that the measurement is failed, and therefore, it is possible to prevent such case by using the other filtrate water observation plates. In such a case, an upper-stream filtrate water observation plate functions as a filter for the lower-stream filtrate water observation plate.

Embodiment 3

Figure 10:
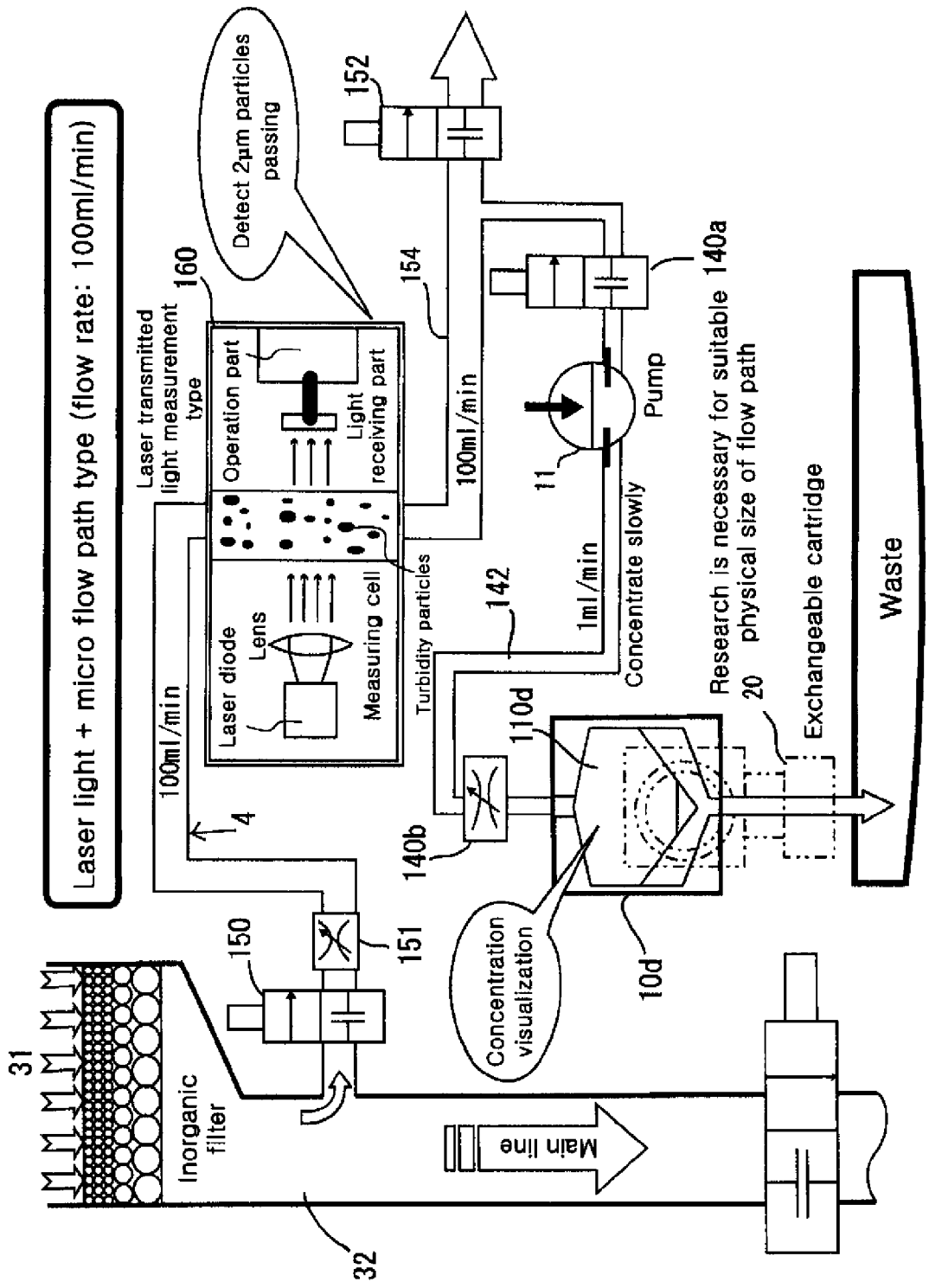
FIG. 10 is a view showing schematically yet another filtrate water monitoring apparatus according to Embodiment 3.

FIG. 10 is a diagram schematically showing Embodiment 3 of the present invention. Redundant descriptions with those in Embodiment 1 or 2 will be omitted. The filtrate water pipe line system 4 is made to branch from the main pipe (main line) through which filtrate water filtrated through the water supply pipe line system 31 passes in the same way as in Embodiments 1 and 2. The gate valve 150 and the throttle valve 151 are installed in the filtrate water pipe line system 4, that prevent the filtrate water from passing through the filtrate water pipe line system 4 or adjust a quantity of the filtrate water. Here, a flow rate of 100 ml/min is provided.

Next, a turbidity meter 160 in a laser transmitted light measurement method is provided. The turbidity meter 160 measures a situation of turbidity by measurement using a laser beam before detecting an image of sample water in the flow channel of the branched filtrate water pipe line system 4.

It is possible to sense occurrence of damage to the membrane filtration in advance due to the turbidity meter 160. The filtrate water discharged from the turbidity meter 160 flows in a pipe 154 at a flow rate of 100 ml/min, and when the throttle valve 152 is not closed, the filtrate water is directly discharged out of the system. When the throttle valve 152 is closed, the filtrate water passes through the branched pipe line system, and passes through a gate valve 140a to flow into the pump 11. The pump 11 compensates for the pressure loss caused in the upstream, and pressurizes so as to make the filtrate water flow toward a filtrate water observation plate 10d. The filtrate water discharged from the pump 11 flows at approximately 1 ml/min in the pipe 142, and is adjusted to be a favorable flow rate through a throttle valve 140b to flow into an observation bath 110d of the filtrate water observation plate 10d. In the filtrate water observation plate 10d, as described above, the impurities in the filtrate water are accumulated, and images of the impurities are shot by the optical device (image shooting means) 20 for measuring shapes thereof, thereby enabling analysis thereof by the image analysis unit (image analysis means) 3 (refer to FIG. 1). Further, the filtrate water discharged from the filtrate water observation plate 10d is wasted after the observation.

Next, the operations of Embodiment 3 will be described. The sample water in the branched filtrate water pipe line system 4 is always measured by the turbidity meter 160. At this time, the gate valve 140a may be closed, and the optical device 20 may be switched off. When the particle amount in the sample water in the flow channel exceeds a given value and a value of the turbidity meter exceeds a preset value, the gate valve 140a is opened, and the optical device 20 is switched on, which allows to start measuring particles by shooting images. The filtrate water observation plate 10d has the feature of micro-level measurement, and it is considered that the analysis of shot images includes time-consuming work such as reference to the database accumulated in the past, the optical device 20 may be preferably made to operate only for a certain period in this way. That is, it is not necessary to always perform the image measurement.

Generally, a turbidity meter is to measure an absolute value of macro particle amount in the flow channel of which flow rate is relatively high, and the image measurement in the flow channel in the observing plate is to measure a state of each particle at the micro level. Accordingly, although it is the disadvantage that it is impossible to perform measurement of all the water samples taken from the membrane filtration water-purifying apparatus by the image measurement serving as the micro measurement means, the micro measurement means can be complemented by the macro measurement means. Macro particle measurement is capable of capturing particles that exist in an uneven manner at lease partially in the flow channel depending on the way of setting a preset value. However, the micro particle measurement may be conducted to a portion where there are no particles (unevenness in sampling). In such case, it is first determined whether particles exist or not by the macro particle measurement. Thereafter, the water is concentrated so as to increase the ratio of those particles accounted in the sample water, which makes the micro measurement possible even by taking the sample water partially. By performing the micro particle measurement even for an extremely small amount of the flowing water, it is possible to stably perform the image measurement even when particles are dispersed locally or uneven in the flowing water or when an extremely small amount of particles exit. As described hereinafter, particles may include substances which can be monitored by the monitoring apparatus in the present embodiment. Such particles may include substances which are substantially insoluble in water, or whose solution velocity is slow. When water is targeted, such particles correspond to impurities.

Further, even if screening measurement with the turbidity meter 160 is performed as a preliminary test, it is not prevented to grasp a special phenomenon such as rupture of the filtration film. A detection level of the turbidity meter 160 can be adjusted such that, when the filtration film is ruptured, an abnormal value is reliably detected by measurement with the turbidity meter 160, and in contrast thereto, when the rupture of the filtration film is not generated, no abnormal value is detected by the measurement with the turbidity meter 160. For detecting the abnormal value in the measurement with the turbidity meter 160, a predetermined threshold may be set, which is appropriately adjustable in the level. That is, provided that the level is set such that it is reliably detected if the filtration film is ruptured and that it can be also detected if there is any possibility of the rupture of the filtration filter, it is possible to detect whether the rupture of the filtration filter occurs or not by more accurate detection means with the filtrate water observation plate 10d against the false alarm.

In this way, provided that screening measurement with the turbidity meter 160 is performed, it is possible to complement the measurement through the filtrate water observation plate 10d, which may be favorable detection means for detecting rupture of the filtration film as a whole. For example, because a large quantity of filtrate water at 100 ml/min can be targeted to measure in screening measurement with the turbidity meter 160, it is possible to more easily prevent errors due to unevenness in sampling. Further, because it is possible to take a sufficient time for measurement through the filtrate water observation plate 10d, it is possible to conduct more precise detection by the filtrate water observation plate 10d.

Figure 11:
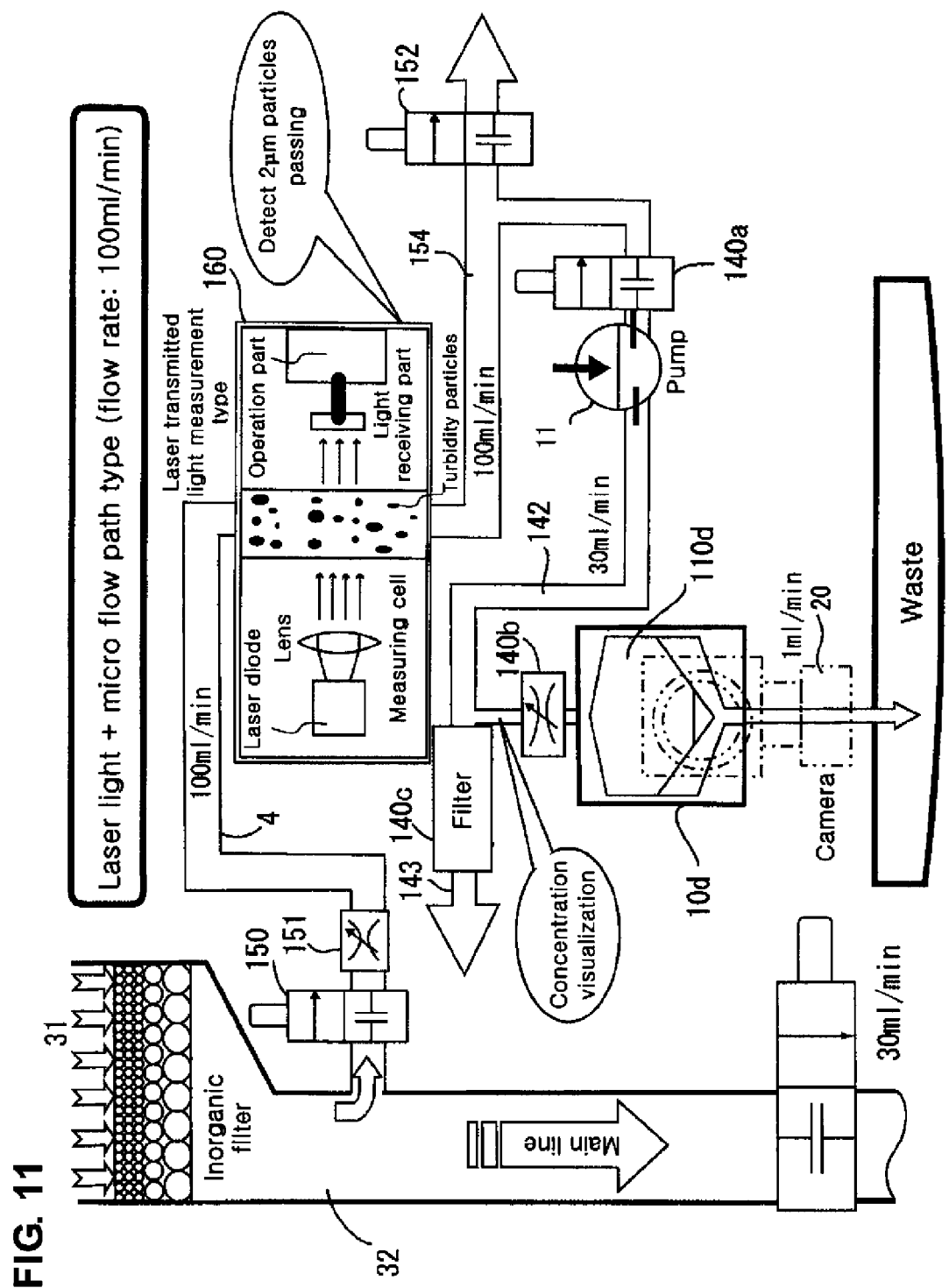
FIG. 11 is a view showing schematically still another filtrate water monitoring apparatus according to Embodiment 4.

FIG. 11 is a diagram schematically showing Embodiment 4, which is improvement from Embodiment 3 of FIG. 10. The basic structure of Embodiment 4 is the same as that of Embodiment 2 of FIG. 10, and redundant descriptions will be omitted. In Embodiment 4, a larger quantity of filtrate water at approximately 30 ml/min is made to flow in the pipe 142 made to branch, and a drain pipe 143 with a filter (physical concentration means) 140c is provided in front of the throttle valve 140b. The impurities are concentrated in front of the filter 140c by the filter 140c, and the filtrate water passes through the throttle valve 140b to flow into the observation bath 110d of the filtrate water observation plate 10d. Accordingly, it is possible to pool impurities of an amount required for observation in the observation bath 110d in a shorter time as compared with Embodiment 3 of FIG. 10. As the physical concentration means, not only the filter 140c, but also agglutinated concentrations of impurities by ultrasonic waves from a ultrasonic transducer, adsorptive concentrations of impurities by micro bubbles from a micro bubble generating device, evaporative concentrations of filtrate water by a heater, or the like may be named.

Figure 12:
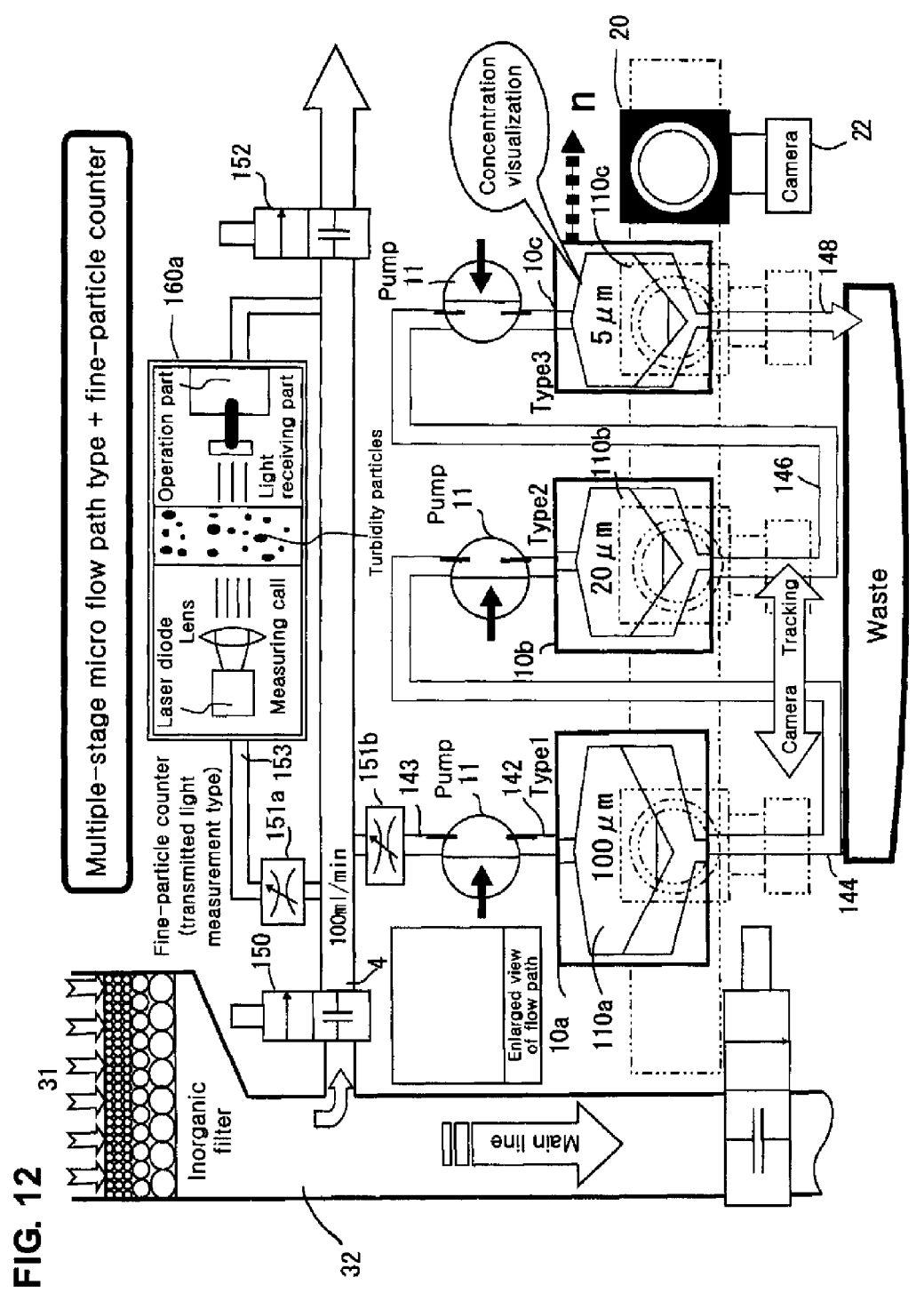

FIG. 12 shows Embodiment 5 which is different from those in Embodiments 2 to 4 shown in FIGS. 9 to 11. However, because the outlines of the configurations and the configurations of the respective components are in common, the redundant descriptions will be omitted. The filtrate water pipe line system 4 is made to branch from the main pipe (main line) through which filtrate water filtrated through the water supply pipe line system 31 passes in the same way as in Embodiments 1 to 4. The gate valve 150 is set in the filtrate water pipe line system 4, and the gate valve 150 prevents the filtrate water from passing through the filtrate water pipe line system 4, or adjusts a flow amount of the filtrate water. Where a flow rate of approximately 100 ml/min is provided, the gate valve 152 is set at a leading part of the filtrate water pipe line system 4, and the filtrate water passing through the gate valve 152 is discharged out of the system.

The filtrate water pipe line system 4 is made to branch into a branch line 153 that guides the filtrate water to a fine-particle counter 160a similar to the turbidity meter 160 in Embodiments 3 and 4, and a branch line 143 that guides the filtrate water to the filtrate water observation plates 10a, 10b, and 10c in Embodiment 2. Throttle valves 151a and 151b capable of adjusting a flow rate are arranged as gate valves in the respective pipes 153 and 143. Differently from the cases in Embodiments 3 and 4, the fine-particle counter 160a is not arrayed upstream of the filtrate water observation plates, but arranged in parallel with those.

The throttle valve 151a is always open, to make a considerable quantity of filtrate water at approximately 100 ml/min of filtrate water flowing into the filtrate water pipe line system 4 flow into the pipe 153. The fine-particle counter is capable of always observing to monitor the filtrate water in the same way as the turbidity meter 160. Because a monitoring threshold by the fine-particle counter and the like are substantially the same as in the case of the turbidity meter 160 described above, the details will be omitted. However, differently from Embodiments 3 and 4, the system is made as a parallel system, the types and concentrations of impurities in water to be observed may differ depending on a difference in sampling. On the other hand, because the turbidity meter 160 is independent in parallel, the turbidity meter 160 is capable of producing independent detected results.

The throttle valve 151b is always opened or by a signal corresponding to a measuring result from the fine-particle counter 160a, to guide the filtrate water flowing into the filtrate water pipe line system 4 into the pipe 143. The first, second, and third filtrate water observation plates 10a, 10b, and 10c respectively have depths of 50 μm, 20 μm, and 2 μm as depths at the shallow part sides of the steps 23. Further, the first, second, and third filtrate water observation plates 10a, 10b, and 10c respectively have depths of 100 μm, 20 μm, and 5 μm as depths at the abyss sides of the steps 23. Accordingly, impurities respectively in predetermined sizes are accumulated in the respective observation baths 110a, 110b, and 110c. The shapes of these impurities are taken as images by the optical device (image shooting means) 20, and the images are analyzed by the image analysis unit (image analysis means) 3 (refer to FIG. 1). At this time, in the same way as Embodiment 2, the optical device 20 is provided to be movable along a rail provided in parallel with the observation baths 110a, 110b, and 110c which are arranged in series, and the optical device 20 is made to move in front of the respective observation baths 110a, 110b, and 110c periodically and/or as needed, to take images. Because the one optical device 20 is used in this way, it is possible to avoid a difference in dimension measuring results on the basis of an individual difference in devices.

Figure 13:
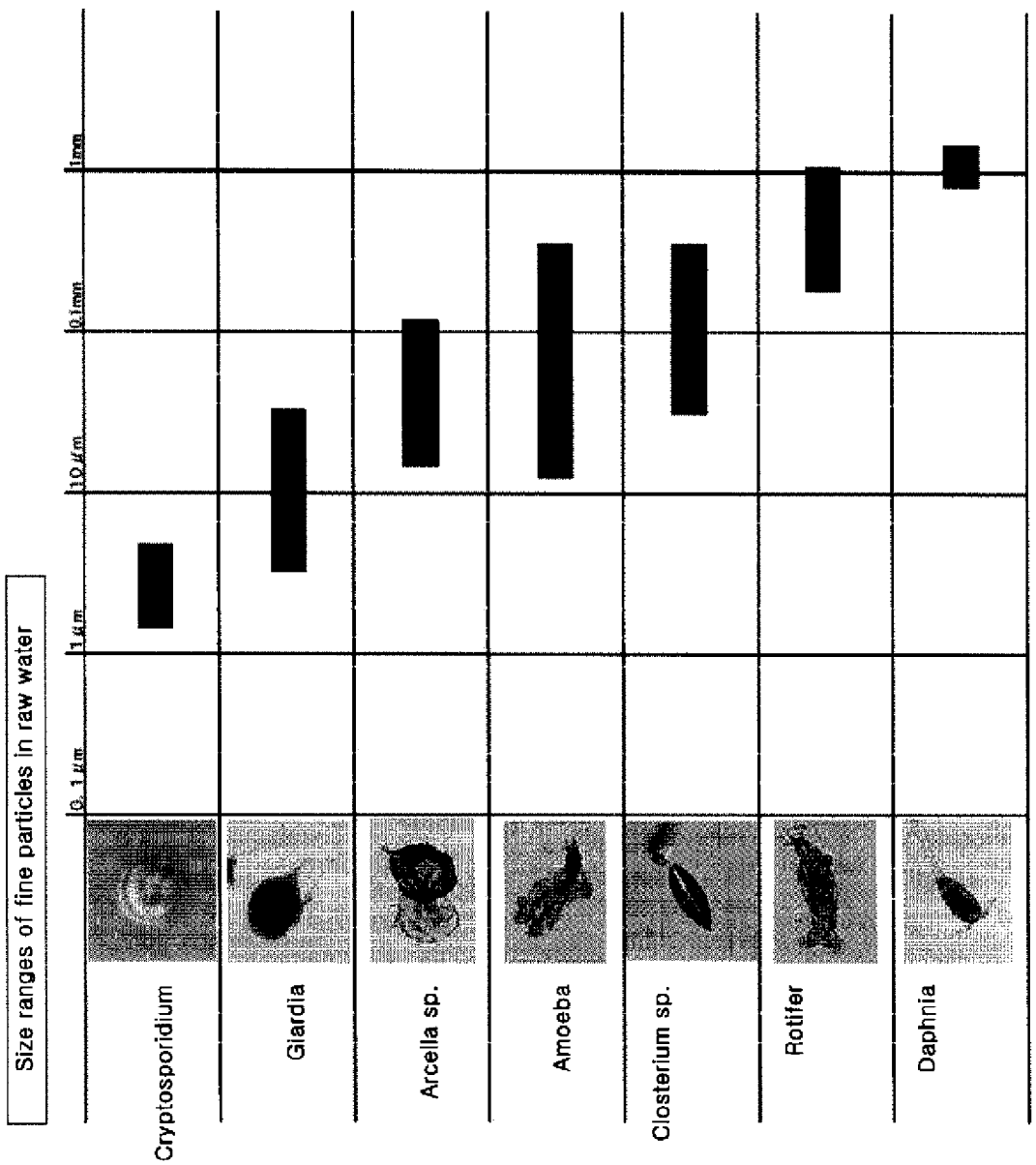
FIG. 13 is a diagram summarizing sizes and shapes of microorganisms and the like contained in raw water.

FIG. 13 shows a table in which sizes and shapes of microorganisms generally included in raw water are organized. As clear from the chart, sizes as impurities differ in accordance with types of microorganisms. Accordingly, types of the respective microorganisms can be further specified by observing shapes of impurities using a plurality of the filtrate water observation plates 10a, 10b, and 10c. For example, when the multiple-stage observation baths of FIG. 12 are used, because Daphnia and Rotifer are 100 μm or more in size, they cannot be put in any observation bath, which cannot be observed. Further, because *Closterium* sp., *Amoeba*, and *Arcella* sp. are approximately 10 μm to 200 μm in size, some of those can be observed in the first observation bath 110a. Further, because *Amoeba, Arcella* sp., and *Giardia* are 20 μm or less and 10 μm or more in size in some cases, some of those can be observed in the second observation bath 110b. Then, because *Giardia* and *Cryptosporidium* are 5 μm or less and 2 μm or more in some cases, some of those can be observed in the third observation bath 110c. Because these microorganisms can be specifically increased and decreased in filtrate water due to rupture of the filtration film, these microorganisms can be observed as a key to detect rupture of the filtration film. On the other hand, these microorganisms directly have an effect on the quality of water in some cases, and the quality of water can always be observed by detecting and observing these microorganisms, which is greatly useful for quality control. Further, types or amounts of microorganisms to be detected may differ depending on the way of rupturing the filtration film, which makes it possible to simultaneously detect rupture of the filtration film by observing those.

Figure 14:
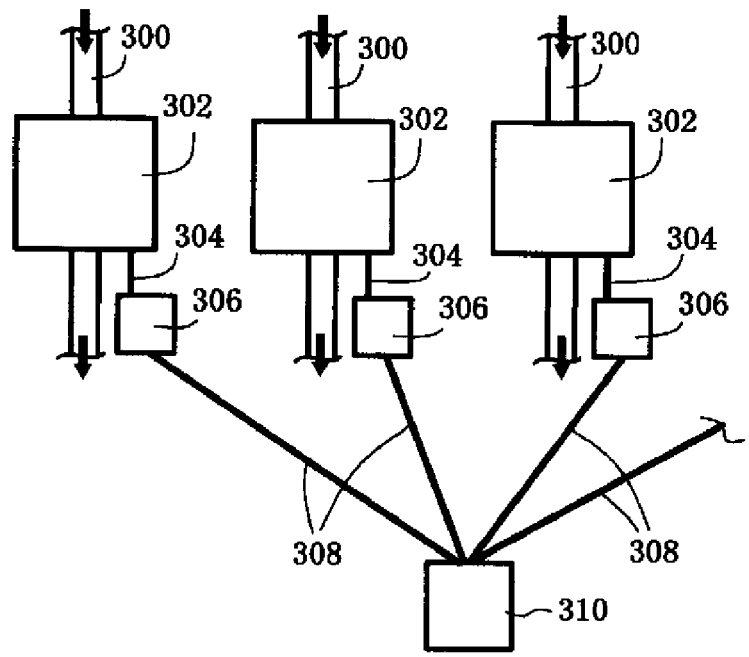
FIG. 14 is a view showing schematically another filtrate water monitoring system of another embodiment.
Figure 15:
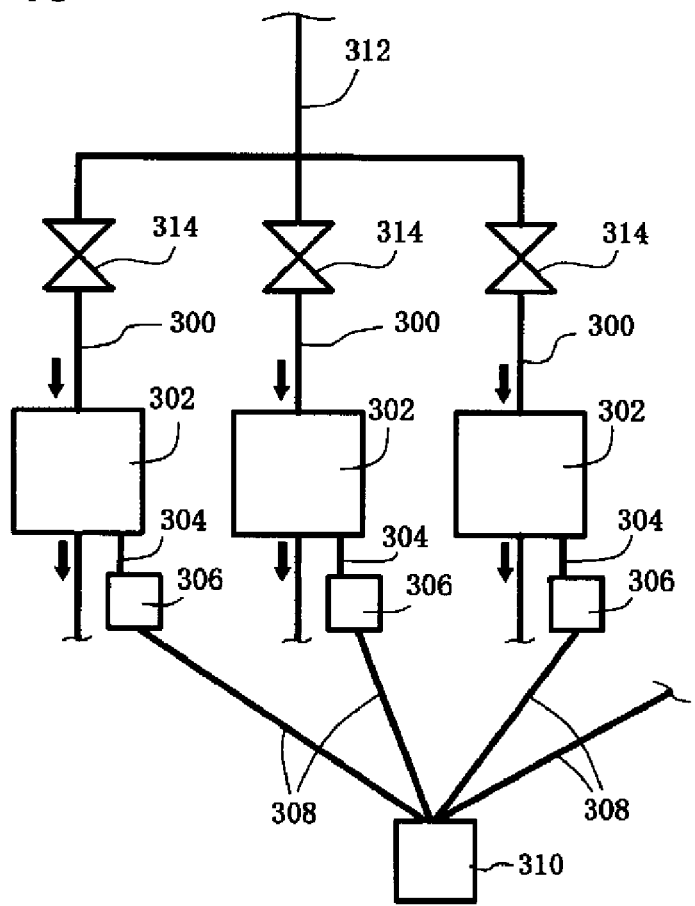
FIG. 15 is a view showing schematically yet another filtrate water monitoring system of yet another embodiment.

FIGS. 14 to 18 respectively show other embodiments. FIG. 14 is a membrane filtration water-purifying system respectively having membrane filtration water-purifying apparatuses capable of simultaneously processing three or more types of raw water. Membrane filtration water-purifying apparatuses 302 respectively have filtrate water sampling/image shooting units connected to pipe lines 304 so as to be able to guide the filtrate water, and are controlled by an analysis/control apparatus 310 via signal communication paths 308. In FIG. 15, in the same way, a plurality of the membrane filtration water-purifying apparatuses 302 respectively have filtrate water sampling/image shooting units connected to the pipe lines 304 so as to be able to guide the filtrate water, and are controlled by the analysis/control apparatus 310 via the signal communication paths 308. Here, one type of raw water is guided from a main pipe line 312, and their flow rates are limited by valves 314 provided to respective pipe lines 300. For example, the three valves may be opened so as to make all the three membrane filtration water-purifying apparatuses 302 shown in the drawing operate. Further, the three membrane filtration water-purifying apparatuses 302 may be made to operate one by one in order according to each maintenance schedule. At this time, one of the three valves 314 is open.

Figure 16:
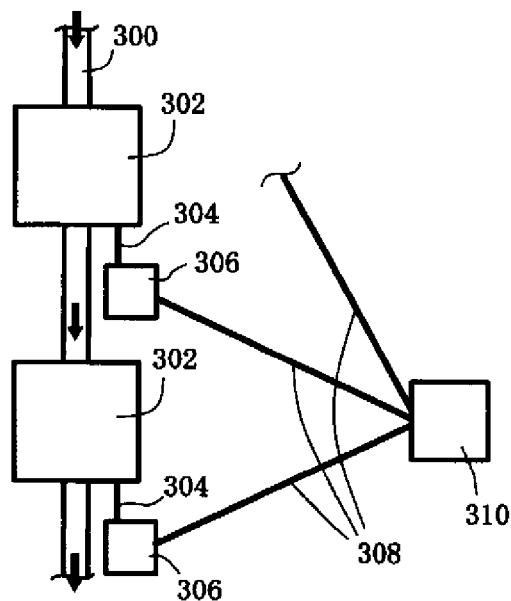
FIG. 16 is a view showing schematically still another filtrate water monitoring system of still another embodiment.

FIG. 16 schematically shows a system in which a plurality of the membrane filtration water-purifying apparatuses 302 are arranged in series from one type of raw water to purify the water. The membrane filtration water-purifying apparatuses 302 respectively have filtrate water sampling/image shooting units connected to the pipe lines 304 so as to guide the filtrate water, and are controlled by the analysis/control apparatus 310 via the signal communication paths 308.

As described above, the present invention has been described by exemplifying the several embodiments. The present invention is not limited thereto. Further, as a matter of course, the present invention may include aspects in which modifications and improvements are added to the embodiments as described above. In particular, the embodiments having one or three filtrate water observation plates have been described. However, the present invention is not limited to those embodiments, and embodiments including more filtrate water observation plates as well may be within the scope of the present invention.

What is claimed is:

1. A filtrate water monitoring apparatus which monitors filtrate water discharged from a membrane filtration water-purifying apparatus, comprising:
    physical detection means for utilizing or detecting a physical phenomenon which varies depending on behavior of particles in the filtrate water flowing in a branch filtrate water pipe line system (hereinafter, called "particles in flowing water") wherein the physical detection means is connected to the branch filtrate water pipe line system branching in order to sample some of the filtrate water as sample water from a filtrate water pipe line system connected to an outlet of the membrane filtration water-purifying apparatus;
    a filtrate water observation cell which is arranged downstream of the physical detection means in the branch filtrate water pipe line system and has a flow channel for letting the filtrate water pass through inside thereof; and image detection means for shooting an image in filtrate water flowing in the flow channel of the filtrate water observation cell and for identifying impurities included in the filtrate water.

2. The filtrate water monitoring apparatus according to claim 1, wherein the physical detection means is a turbidity meter with a laser beam.

3. The filtrate water monitoring apparatus according to claim 1, wherein the physical detection means is a fine-particle counter with a laser beam.

4. The filtrate water monitoring apparatus according to claim 1, comprising:
an openable and closable valve disposed between the physical detection means and the filtrate water observation cell in the branch filtrate water pipe line system such that the filtrate water flows into the filtrate water observation cell when the physical detection means detects a greater number of particles in the flowing water than a predetermined number.

5. The filtrate water monitoring apparatus according to claim 4, wherein the image detection means identifies the particles in the flowing water after a predetermined period of time from when the physical detection means detects the greater number of particles in the flowing water than the predetermined number.

6. The filtrate water monitoring apparatus according claim 1, comprising:
physical concentration means for increasing density of the particles in the flowing water that flows into the filtrate water observation cell, the physical concentration means disposed between the physical detection means and the filtrate water observation cell in the branch filtrate water pipe line system.

7. The filtrate water monitoring apparatus according to claim 1
wherein the filtrate water observation cell has an observation bath through which flow of the filtrate water is observed in the flow channel, and a plurality of filtrate water observation cells are arranged in series along the branch filtrate water pipe line system.

8. The filtrate water monitoring apparatus according to claim 1
wherein the filtrate water observation cell has an observation bath through which flow of the filtrate water is observed in the flow channel, and a plurality of observation baths are arranged in series along the flow channel.

9. The filtrate water monitoring apparatus according to claim 1, wherein a porous plate with pores is disposed so as to block the flow channel.

10. The filtrate water monitoring apparatus according to claim 7, wherein the observation bath has a step to decrease a cross-sectional area of the flow channel along the flow channel.

11. The filtrate water monitoring apparatus according to claim 10, wherein a plurality of observation baths are arranged and connected in series, and the cross-sectional area of the flow channel, which is made smaller by the step, become gradually smaller along the flow of the filtrate water.

12. The filtrate water monitoring apparatus according to claim 8, wherein the image detection means is provided in a movable way so as to be capable of shooting an image in the filtrate water flowing in any one of the plurality of observation baths.

13. The filtrate water monitoring apparatus according to claim 10, wherein the step is provided in a V-shape as viewed in a plan view so as to be capable of separating or observing the particles in the flowing water based on difference in density of the particles in the flowing water in the filtrate water observation cell.

14. A filtrate water monitoring system comprising: a plurality of membrane filtration water-purifying apparatuses and a filtrate water monitoring apparatus that monitors filtrate water filtrated through each of the membrane filtration water-purifying apparatuses, the filtrate water monitoring system comprising:
filtrate water pipe line systems connected respectively to outlets of the plurality of membrane filtration water-purifying apparatuses;
branch filtrate water pipe line systems respectively connected to the filtrate water pipe line systems, the branch filtrate water pipe line systems sampling part of the filtrate water as sample water from the filtrate water pipe line systems;
physical detection means for utilizing or detecting a physical phenomenon which varies depending on behavior of particles in the filtrate water flowing in the branch filtrate water pipe line systems wherein the physical detection means is connected to the branch filtrate water pipe line systems branching in order to sample some of the filtrate water as sample water from the filtrate water pipe line systems connected to the outlets of the membrane filtration water-purifying apparatuses;
a filtrate water observation cell connected to a midpoint of at least one pipe line system in the branch filtrate water pipe line systems, and the filtrate water observation cell having a flow channel in which the filtrate water flows; and
image detection means for shooting an image in filtrate water flowing in the flow channel of the filtrate water observation cell, and for identifying particles in the flowing water included in the filtrate water,
wherein the filtrate water observation cell has an observation bath through which flow of the filtrate water is observed in the flow channel.

15. The filtrate water monitoring system according to claim 14
wherein the observation bath has a step to decrease a cross-sectional area of the flow channel along the flow channel.

16. The filtrate water monitoring system according to claim 14
wherein a porous plate with pores is disposed so as to block the flow channel.

17. The filtrate water monitoring system according to claim 14, wherein a plurality of observation baths are arranged and connected in series along each of the branch filtrate water pipe line systems.

18. The filtrate water monitoring system according to claim 14, wherein a plurality of observation baths are arranged and connected in series along the flow channel.

* * * * *